United States Patent
Wallner

(12) 
(10) Patent No.: US 6,355,614 B1
(45) Date of Patent: Mar. 12, 2002

(54) CYCLIC BOROPROLINE COMPOUNDS

(75) Inventor: Barbara P. Wallner, Weston, MA (US)

(73) Assignee: Point Therapeutics, Boston, MA (US)

( * ) Notice: Subject to any disclaimer, the term of this patent is extended or adjusted under 35 U.S.C. 154(b) by 0 days.

(21) Appl. No.: 09/312,565

(22) Filed: May 14, 1999

Related U.S. Application Data

(60) Provisional application No. 60/088,540, filed on Jun. 5, 1998.

(51) Int. Cl.[7] ............................................. A61K 38/00
(52) U.S. Cl. ..................... 514/10; 514/249; 514/253.09
(58) Field of Search ...................... 514/10, 249, 253.09

(56) References Cited

U.S. PATENT DOCUMENTS

| | | | |
|---|---|---|---|
| 4,318,904 A | 3/1982 | Shaw et al. | 424/177 |
| 4,443,609 A | 4/1984 | Oude Alink et al. | 548/111 |
| 4,499,082 A | 2/1985 | Shenvi et al. | 514/2 |
| 4,582,821 A | 4/1986 | Kettner et al. | 514/18 |
| 4,636,492 A | 1/1987 | Kettner et al. | 514/18 |
| 4,644,055 A | 2/1987 | Kettner et al. | 530/330 |
| 4,652,552 A | 3/1987 | Kettner et al. | 514/18 |
| 4,935,493 A | 6/1990 | Bachovchin et al. | 530/331 |
| 4,963,655 A | 10/1990 | Kinder et al. | 530/531 |
| 5,093,477 A | 3/1992 | Mölling et al. | 530/328 |
| 5,187,157 A | 2/1993 | Kettner et al. | 514/18 |
| 5,215,926 A | 6/1993 | Etchells, III et al. | 436/501 |
| 5,242,904 A | 9/1993 | Kettner et al. | 514/18 |
| 5,250,720 A | 10/1993 | Kettner et al. | 558/228 |
| 5,288,707 A | 2/1994 | Metternich | 514/19 |
| 5,296,604 A | 3/1994 | Hanko et al. | 546/169 |
| 5,329,028 A | 7/1994 | Ashkenzi et al. | |
| 5,378,624 A | 1/1995 | Berenson et al. | 435/239 |
| 5,384,410 A | 1/1995 | Kettner et al. | 548/405 |
| 5,444,049 A | 8/1995 | de Nanteuil et al. | 514/18 |
| 5,462,928 A | 10/1995 | Bachovchin et al. | 514/19 |
| 5,506,130 A | 4/1996 | Peterson et al. | 435/240.1 |
| 5,527,923 A | 6/1996 | Klingler et al. | 548/570 |
| 5,543,396 A | 8/1996 | Powers et al. | 514/19 |
| 5,554,728 A | 9/1996 | Basava et al. | 530/327 |
| 5,635,386 A | 6/1997 | Palsson et al. | 435/372 |
| 5,635,387 A | 6/1997 | Fei et al. | 435/378 |
| 5,646,043 A | 7/1997 | Emerson et al. | 435/373 |

FOREIGN PATENT DOCUMENTS

| | | |
|---|---|---|
| EP | 0356223 A2 | 2/1990 |
| EP | 0471651 A2 | 2/1992 |
| EP | 0420913 B1 | 11/1995 |
| WO | WO89/03223 | 4/1989 |
| WO | WO91/16339 | 10/1991 |
| WO | WO91/17767 | 11/1991 |
| WO | WO92/12140 | 7/1992 |
| WO | WO92/17490 | 10/1992 |
| WO | WO93/02057 | 2/1993 |
| WO | WO93/05011 | 3/1993 |
| WO | WO93/08259 | 4/1993 |
| WO | WO93/10127 | 5/1993 |
| WO | WO93/16102 | 8/1993 |
| WO | WO94/03055 | 2/1994 |
| WO | WO94/09132 | 4/1994 |
| WO | WO94/20526 | 9/1994 |
| WO | WO97/25873 | 11/1994 |
| WO | WO94/28915 | 12/1994 |
| WO | WO94/29335 | 12/1994 |
| WO | WO95/11689 | 5/1995 |
| WO | WO95/12618 | 5/1995 |
| WO | WO95/15309 | 6/1995 |
| WO | WO95/29190 | 11/1995 |
| WO | WO95/29691 | 11/1995 |
| WO | WO95/34538 | 12/1995 |
| WO | WO96/40263 | 12/1996 |
| WO | WO96/40858 | 12/1996 |
| WO | WO 98/00439 | 1/1998 |
| WO | WO 98/50046 | 11/1998 |

OTHER PUBLICATIONS

Simon J. Coutts et al., "Structure—Activity Relationships of Boronic Acid Inhibitors of Depeptidyl Peptidase IV. 1. Variation of the $P_2$ Position of $X_{aa}$–boroPro Depeptides," *J. Med. Chem.* 1996, vol. 39, No. 10, pp. 2087–2094.

Abstract to coutts, S. J. et al., "Structure–Activity Relationships of Boronic Acid Inhibitors of Dipeptidyl Peptidase IV. 1. Variation of the P2 Position of Xaa–boroPro Dipeptides", J. Med. Chem. 39(10), pp. 2087–2094, 1996.*

Abstract to Kelly, et al., "Immunosupressive boronic acid depeptides: correlation between conformation and activity", J. Am. Chem. Soc. 115(26), pp. 12637–12638, 1993.*

Colowick, S., et al., "Methods in Enzymology", pp. 220–225, 1993.

Cordes, E., et al., "Transition States for Hydrolysis of Acetals, Ketals Glycosides, and Glycosylamines", Chaper 11, pp. 429–465, 1994.

Thompson, R., "Use of Peptide Aldehydes to Generate Transition–State Analogs of Elastase", *Biochemistry*, (1973), 12:1:47–51.

Baugh, R., et al., "Proteinases and Tumor Invasion", (1980), 165:157–179.

Bodanszky, M., "Principles of Peptide Synthesis", *Springer–Verlag*, (1984), vol. 16.

(List continued on next page.)

*Primary Examiner*—Dwaynes C. Jones
(74) *Attorney, Agent, or Firm*—Wolf, Greenfield & Sacks, P.C

(57) ABSTRACT

Substantially pure preparations of cyclic boroProline compounds that bind, in cyclic or linear form, to CD26 are provided. Methods for using the cyclic compounds to stimulate the activation and/or proliferation of immune cells to achieve preselected normal in vivo levels of these cells also are provided. Evidence of the oral bioavailability and activity of a preferred cyclic compound, valine-prolineboronic acid (ValboroPro), also is provided.

8 Claims, 6 Drawing Sheets

OTHER PUBLICATIONS

Bodanszky, M., "The Practice of Peptide Synthesis", Springer–Verlag, (1984), vol. 21.
Matteson, D., et al., "Synthesis and Properties of Pinanediol α–Amido Boronic Esters" Organometallics, (1984), 3:1284–1288.
Powers, C., et al., "Elastase Inhibitors for Treatment of Emphysema—NHLBI Workshop Summary" US Dept. of Health and Human Services, (1985), 1097–1100.
Yoshimoto, T., et al., "Comparison of Inhibitory Effects of Prolinal–Containing Peptide Derivates on Prolyl . . . ", (1985), 98:975–979.
Kettner, C.A., et al., "Kinetic Properties of the Binding of Alpha–Lytic Protease to Peptide Boronic Acids", Biochemistry, (1988), 27:7682–7688.
Tam, J.P., "Synthetic Peptide Vaccine Design: Synthesis and Properties of a High–Density Multiple Antigenic Peptide System", Proc Natl Acad Sci USA, (1988), 85:5409–5413.
Bailey, P.D., "An Introduction to Peptide Chemistry", Wiley Publishers, (1990), 1–81.
Kettner, C.A. and Shenvi, A.B., "Peptide Boronic Acid Inhibitors of Trypsin–Like Proteases, Their Preparation and Use as Anticoagulants and Inflammation Inhibitors", Chemical Abstract Onlys, (1990), 112:80 (91790c).
Bachovchin, W.W., et al., "Inhibition of IGA1 Proteinases From Neisseria Gonorrhoeae and Hemophilus Influenzae by Peptide Prolyl Boronic Acids", J Biol Chem, (1990), 265: 3738–3743.
Kinder, D.H., et al., "Analogues of Carbamyl Aspartate as Inhibitors of Dihydroorotase: Preparation of Boronic Acid Transition–State Analogues and a Zinc Chelator Carbamylhomocysteine", J Med Chem, (1990), 33:819–823.
Flentke, G.R., et al., "Inhibition of Dipeptidyl Aminopeptidase IV (DP–IV) by XAA–Boropro Dipeptides and Use of These Inhibitors to Examine the Role of DP–IV in T–Cell Function", Proc Natl Acad Sci USA, (1991), 88:1556–1559.
Schon, E., et al., "Dipeptidyl Peptidase IV in the Immune System", Biol Chem Hoppe–Seyler, (1991), 372:305–311.
Kubota, T., et al., "Involvement of Dipeptidyl Peptidase IV in an in Vivo Immune Response", Clin Exp Immunol, (1992), 89:192–197.
Gutheil, W.G., et al., "Separation of L–Pro–DL–Boropro Into its Component Diastereomers and Kinetic Analysis of Their Inhibition of Dipeptidyl Peptidase IV. A New Method For the Analysis of Slow, Tight–Binding Inhibition", Biochemistry, (1993), 32:8723–8731.
Kelly, T.A., et al., "Immunosuppressive Boronic Acid Dipeptides: Correlation Between Conformation and Activity", J Am Chem Soc, (1993), 115:12637–12638.
Songyang, Z., et al., "SH2 Domains Recognize Specific Phosphopeptide Sequences", Cell, (1993), 72:767–778.
Subramanyam, M., et al., "Mechanism of HIV–1 Tat Induced Inhibition of Antigen–Specific T Cell Responsiveness", J Immunol, (1993), 150:2544–2553.
Demuth, H.U., et al., "Design of (Omega–N–(O–Acyl)Hydroxy Amid) Aminodicarboxylic Acid Pyrrolidides as Potent Inhibitors of Proline–Specific Peptidases", FEBS Lett, (1993), 320:23–27.
Janeway, C., et al., "Immunobiology—The Immune System in Health and Disease", Current Biology LTD, (1994), Chapter 12, pp. 1–35.
Brady, L., and Dodson, G., "Reflections of a Peptide", Nature, (1994), 368:692–693.

Nicola, N, et al., "Guidebook to Cytokines and Their Receptors", Sambrook and Tooze Publication, (1994), pp. 1–257.
Perstorp Biotec Company, "Molecular Biology Catalog", (1994).
Jameson, B.A., et al., "A Rationally Designed CD4 Analogue Inhibits Experimental Allergic Encephalomyelitis", Nature, (1994), 368:744–746—Abstract Only.
Mosmann, T.R., "Cytokine Patterns During the Progression to Aids" Science, (1994), 265:193–194.
Seed, B., "Making Agonists of Antagonists", Chemistry & Biology, (1994), 1:125–129.
Austin, D.J., et al., "Proximity Versus Allostery the Role of Regulated Protein Dimerization in Biology", Chemistry & Biology, (1994), 1:131–136.
Sudmeier, J.L., et al., "Solution Structures of Active and Inactive Forms of the DP IV (CD26) Inhibitor Pro–Boropro Determined by NMR Spectroscopy", Biochemistry, (1994), 33:12427–12438.
Kubota, T., et al., "Dipeptidyl Peptidase IV (DP IV) Activity in Serum and on Lymphocytes of MRL/Mp–lpr/lpr Mice Correlates with Disease Onset", Clin Exp Immunol, (1994), 96:292–296.
Snow, R.J., et al., "Studies on Proline Boronic Acid Dipeptide Inhibitors of Dipeptidyl Peptidase IV: Identification of a Cyclic Species Containing A B–N Bond", J. Am. Chem Soc, (1994), 116:10860–10869.
Günther, U.L., et al., "Solution Structures of the DP IV (CD26) Inhibitor Val–BoroPro Determined by NMR Spectroscopy", Magnetic Resonance in Chem, (1995), 33:959–970.
Subramanyam, M., et al., "CD26, AT–Cell Accessory Molecule Induction of Antigen–Specific Immune–Suppression by Inactivation of CD26: A Clue To the Aids Paradox?", in Dipeptidyl Peptidase IV(CD26) in Metabolism and Immune Response, (1995), Ed. B. Fleischer: 155–162.
Schmitz T, et al., "Potentiation of the Immune Response in HIV–1+ Individuals", J Clin Invest, (1996), 97:1545–1549.
Aguila, H.L., et al., "From Stem Cells to Lymphocytes: Biology and Transplantation", Immun Rev, (1997), 157:13–40.
Dupont, B., "Immunology of Hematopoietic Stem Cell Transplantation: A Brief Review of Its History", Immun Rev, (1997), 157:5–12.
Bodansky, M., "Peptide Chemistry, A Practical Textbook", Springer–Verlag, (1988) 1–9.
Boros, L.G., et al., "Fluoroolefin Peptide Isosteres–Tools for Controlling Peptide Conformations", Tetrahedron Letters, (1994), 35:6033–6036.
Goodman, M., and Chorev, M., "On the Concept of Linear Modified Retro–Peptide Structures", Accounts of Chemical Research, (1979), 12:1–7.
Guichard, G., et al., Partially Modified Retro–Inverso Pseudopeptides as Non–Natural Ligands for the Human Class I Histocompatibility Molecule HLA–A2, J Med Chem, (1996), 39:2030–2039.
Jardetzky, T.S., et al., Three–Dimensional Structure of a Human Class II Histocompatibility Molecule Complexed with Superantigen, Nature, (1994), 368:711–718.
Zimmerman, D.H., et al., "A New Approach to T–Cell Activation: Natural and Synthetic Conjugates Capable of Activating T Cells", Vaccine Res, (1996), 5:91–102.
Zimmerman, D.H., et al., "Immunization with Peptide Heteroconjugates Primes A T Helper Cell . . . " Vaccine Res, (1996), 5:103–118.

Welch, J.T., and Lin J., Fluoroolefin Containing Dipeptide Isoteres as Inhibitors of Dipeptidyl Peptidase IV (CD26), *Tetrahedron,* (1995), 52:291–304.

Duke–Cohan, J.S., et al., "Targeting of an Activated T–Cell Subset Using a Bispecific Antibody–Toxin Conjugatedirected Against CD4 and CD26", *Blood,* (1993), 82:2224–2234. (Abstract Only).

Kameoka, J., et al., "Direct Association of Adenosine Deaminase with A T Cell Activation Antigen, CD26", *Science,* (1993), 261:466–469. (Abstract only).

Hegen, M., et al., "Function of Dipeptidyl Peptidase IV (CD26, TP103) in Transfected Human T Cells", *Cell Immunol,* (1993), 146:249–260, (Abstract Only).

Hegen, M., et al., "Enzymatic Activity of CD26 (Dipeptidylpeptidase IV) is Not Required for Its Signalling Function in T Cells", *Immunobiology,* (1993), 189:483–493. (Abstract Only).

Tanaka, T., et al., "The Costimulatory Activity of the CD26 Antigen Requires Dipeptidyl Peptidase IV Enzymatic Activity", *Proc Natl Acad Sci U S A,* (1993), 90:4586–4590, (Abstract Only).

Tanaka, T., et al., "Cloning and Functional Expression of the T Cell Activation Antigen CD26", *J Immunol,* (1992), 149:481–486, (Abstract Only).

Scharpe, S., et al., "Purified and Cell–Bound CD26: Enzymatic Inhibition, Antibody Binding Profile, and Expression of T Cells in Relation to Other Surface Markers", *Verh K Acad Geneeskd Belg,* (1994), 56:537–559. (Abstract Only).

Kameoka, J., et al., "Differential CD26–Mediated Activation of the CD3 and CD2 Pathways After CD6–Depleted Allogeneic Bone Marrow Transplantation", *Blood,* (1995), 85:1132–1137. (Abstract.

Mittrucker, H.W., et al., "The Cytoplasmic Tail of the T Cell Receptor Zeta Chain is Required for Signaling Via CD26", *Eur J Immunol,* (1995), 25:295–297. (Abstract Only).

Morimoto, C., et al., 1F7 "A Novel Cell Surface Molecule, Involved In Helper Function of CD4 cells", *J. Of Im Immunol.* 143:34030–3439 (1989) and published erratum appears in *J. Immunology* 144 (5):2027 (Mar. 1990). Abstract Only.

Barton, R.W.J., et al., "Binding Of The T Cell Activation Monoclonal Antibody Tal To Dipeptidyl Peptidase IV", *J. Of Leukocyte Biology* 48:291–296 (1990). Abstract Only.

Bristol, L.A., et al., "Thymocyte Costimulating Antigen Is CD26 (Dipeptidyl–Peptidase IV), Co–stimulation Of Granulocyte, Macrophage, T Lineage Cell Proliferation Via CD26," *J. Of Immunol.* 149:367–372 (1992). Abstract.

Bristol, L.A., et al., "Characterization Of A Novel Thymocyte Costimulating Antigen By The Monoclonal Monoclonal Antibody 1.3", *J. Of Immunol.* 148:332–338 (1992). Abstract Only.

Fleisher, B., et al., "Triggering Of Cytotoxic T Lymphocytes And NK Cells Via The Tp103 Pathway Is Dependent On the Expression Of The T Cell Receptor CD3 Complex", *J. Of Immunol.* 141:1103–1107, Abstract, 1994.

Hegen, M., et al., "The T Cell Triggering Molecule Tp103 . . . " *J. Immunol.* 144:2980–2914 (1990). Abstract Only.

Darmoul, D., et al., "Dipeptidyl Peptidase IV (CD26) Gene Expression In Enterocyte–like Colon Cancer Cell Lines HT–29 And Caco–2: Cloning Of The Complete Human Coding Sequence And Changes Of Dipeptidyl Peptidase IV mRNA Levels During Cell Differentiation," *J. Of Biological Chemistry* 267:220–2208 (1992) Abstract Only.

Tanaka, T., et al., "Cloning And Functional Expression Of The T Cell Activation Antigen CD26", *J. Of Immunol Immunol.* 149: 481–486 (1992); published erratum appears in *J. Immunol.* 50(5): 2090 (Mar. 1993). Abstract Only.

Heins, J., et al., "Mechanism Of Proline–Specific Proteinases: (I) Substrate Specificity of Dipeptidyl Peptidase Peptidase IV From Pig Kidney And Proline–Specific Endopeptidase From Flavobacterium Meningosepticum" *Biochimica Et Biophysica Acta* 954:161–169 (1988). Abstract Only.

Schon, E., et al., "Dipeptidyl Peptidase IV In The Immune System. Effects of Specific Enzyme Inhibitors On On Activity Of Dipeptidyl Peptidase IV And Proliferation Of Human Lymphocytes", *Biological Chemistry Hoppe Seyler* 372:305–311 (1991). Abstract Only.

Schon, E., et al., "The Dipeptidyl Peptidase IV, A Membrane Enzyme Involved In The Proliferation . . . Lymphocytes", *Biomedica Biochimica Acta* 44 (1985). Abstract Only.

Schon, E., et al., "Dipeptidyl Peptidase IV In Human T Lymphocytes. An Approach To The Role Of A Membrane Peptidase In The Immune System" *Biomedica Biochimica Acta* 45:1523–1528 (1986) Abstract Only. Abstract Only.

Schon, E., et al., "The Role Of Dipeptidyl Peptidase IV In Human T Lymphocyte Activation. Inhibitors And Antibodies Against Dipeptidyl Peptidase IV Suppress Lymphocyte Proliferation And Immunoglobulin Synthesis In Vitro" *Eur. J. Of Immunol.* 17:1821–1826 (1987). Abstract Only.

Freeman, et al., "*Clinical & Experimental Immunology*" 88 (2): 275–279 (May 1992). Abstract Only.

Perry, et al., *Eur. J. Of Immunol.* 26 (1): 136–141 (Jan. 1996). Abstract Only.

Goodstone, et al., *Annals Of The Rheumatic Diseases* 55(1):40–46 (Jan. 1996). Abstract Only.

Hall, et al., *Seminars In Dermatology,* 10 (3):240–245 (Sep. 1991). Abstract Only.

Karges, et al., *Molecular Aspects Of Medicine* 16(2):29–213 (1995). Abstract Only.

Short, et al., *Nephrol Dial Transplant* (Supp. 1) pp. 1–121 (1992). Abstract Only.

Kalluri, et al., *J. Of The American Society Of Nephrology* 6(4):1178–1185 (Oct. 1995). Abstract Only.

Mullins, et al., *J. Of Clinical Investigation* 96 (1): 30–37 (Jul. 1996), Abstract Only.

El Far, et al., *J. Of Neurochemistry,* 64 (4): 1696–1702 (Apr. 1995). Abstract Only.

James, et al., *Clinical & Experimental Rheumatology,* 13 (3):299–305 (May–Jun. 1995). Abstract Only.

Van Noort, et al., *Nature* 375 (6534):798–801 (Jun. 29, 1995). Abstract Only.

Protti, et al., *Immunol. Today* 14 (7): 363–368 (Jul. 1993). Abstract Only.

Linington, et al., *Eur. J. Of Immunol.* 22 (7): 1813–1817 (Jul. 1992). Abstract Only.

Chan, et al., *Archives Of Ophthalmology* 113 (5): 597–600 (May 1995). Abstract Only.

Liu, et al., *J. Of Immunol.* 155 (11): 5449–5454 (Dec. 1995). Abstract Only.

Uibo, et al., *J. Of Autoimmunity* 7 (3): 399–411 (Jun. 1994). Abstract Only.

Kokawa, et al., *Eur. J. Of Hematology* 50 (2): 74–80 (1993). Abstract Only.

Daw, et al., *J. Of Immunol.* 156 (2): 818–825 (Jan. 15, 1996). Abstract Only.

Chazenblak, et al., *J. Of Clinical Investigation* 92 (1):62–74 (Jul. 1993). Abstract Only.

Hart, et al., *Pharmaceutical Biotechnology* 6:821–845 (1995). Abstract Only.
Lopez, et al., *Vaccine* 12 (7):585–591 (1994). Abstract Only.
Reynolds, et al., *J. Of Immunol.* 152 (1):193–200 (Jan. 1, 1994). Abstract Only.
Nardelli, et al., *J. Of Immunol.* 148 (3): 914–920 (Feb. 1, 1992). Abstract Only.
Darcy, et al., *J. Of Immunol.* 149 (11):3636–3641 (Dec. 1, 1992). Abstract Only.
Ritu et. al., *Vaccine* 10 (11): 761–765 (1992). Abstract Only.
Ikagawa, et al., *J. Of Allergy & Clinical Immunol.* 97 (1 Pt 1): 53–64 (Jan. 1996). Abstract Only.
Brander, et al., *J. Of Immunol.* 155 (5):2670–2678 (Sep. 1, 1995). Abstract Only.
O'Brien, et al., *Immunology* 86 (2):176–182 (Oct. 1995). Abstract Only.
Zhu et al., *J. Immunol* 155(10), pp. 5064–5073 (Nov. 1995). Abstract Only.
Dudler, et al., *Eur. J. Of Immunol.* 25 (2):538–542 (Feb. 1995). Abstract Only.
Bungy, et al., *Eur. J. Of Immunol.* 24 (9):2098–2103 (Sep. 1994). Abstract Only.
Shimoio, et al., *Int'l. Archives Of Allergy & Immunol.* 105 (2):155–161 (Oct. 1994). Abstract Only.
Kelly, T.A., et al., "The Efficient Synthesis And Simple Resolution Of A Proline Boronate Ester Suitable For Enzyme Inhibition Studies", *Tetrahedron* 49:1009–1016 (1993). Abstract Only.
Watson, J.D., "Continuous Proliferation Of Murine Antigen Specific Helper T Lymphocytes In Culture", *J. Of Experimental Medicine* 150:1510 (1979). Abstract Only.
Kuchroo, V.K., et al., "Induction Of Experimental Allergic Encephalomyelitis By Myelin Proteolipid–Protein–Specific T Cell Clones And Synthetic Peptides", *Pathobiology* 59:305–312 (1991). Abstract Only.
Kuchroo, V.K., et al., "T–cell Receptor Alpha Chain Plays a Critical Role In Antigen–Specific Suppressor Cell Function", *Proceedings Of The Nat'l. Academy Of Sciences Of The United States Of America* 88:8700 88:8700–8704 (1991). Abstract Only.
Kuchroo, V.K., et al., "Experimental Allergic Encephalomyelitis Medicated By Cloned T Cells Specific For A Synthetic Peptide of Myelin Proteolipid Protein. Fine Specificity And T Cell Receptor V Beta Usage", *J. Of Immunol.* 148:3776–3782 (1992). Abstract Only.
Kuchroo, V.K., et al., "Cytokines And Adhesion Molecules Contribute To The Ability Of Myelin Proteolipid Protein––Specific T Cell Clones To Mediate Experimental Allergic Encephalomyelitis", *J. Of Immunol.* 151:4371–4382 (1993). Abstract Only.
Kuchroo, V.K., et al., "T Cell Receptor (TCR) Usage Determines Disease Susceptibility In Experimental Autoimmune Encephalomyelitis: Studies with TCR V Beta .2 Transgenic Mice", *J. Of Experimental Medicine* 179:1659–1664 (1994). Abstract Only.
Kuchroo, V.K. et al., "A Single TCR Antagonist Peptide Inhibits Experimental Allergic Encephalomyelitis Mediated By A Diverse T Cell Repertoire", *J. Of Immunol.*, 153:3326–3336 (1994). Abstract Only.
Jorgensen, J.L., et al., "Molecular Components Of T–Cell Recognition," *Annu. Rev. Immunol.* 10:835–873 (1992). Abstract Only.

Wyse–Coray, T., et al., "Use Of Antibody/Peptides Constructs Of Direct Antigenic Peptides To T Cells: Evidence For T Cells Processing And Presentation", *Cellular Immunol.*, 139 (1):268–73 (1992). Abstract Only.
Panina–Bordignon, P., et al., "Universally Immunogenic T Cell Epitopes; Promiscuous Binding To Human MHC MHC Class II And Promiscuous Recognition by T Cells", *Eur. J. Immunol.* 19:2237–2242 (1989). Abstract Only.
Ebenbichler, C., et al., "Structure–function Relationships Of The HIV–1 Envelope V3 Loop Tropism Determinant: Evidence For Two Distinct Conformations", *Aids* 7:639–46 (1993). Abstract Only.
Linsley, P.S., et al., "Effects Of Anti–gp120 Monoclonal Antibodies On CD4 Receptor Binding By The Env Protein Of Human Immunodeficiency Virus Type 1", *J. Of Virology* 62:3695–3702 (1988). Abstract Only.
Rini, J.M., et al., "Crystal Structure Of A Human Immunodeficiency Virus Type 1 Neutralizing Antibody, 50.1, In Complex With Its V3 Loop Peptide Antigen", *Proceedings Of The Nat'l. Academy Of Sciences Of The United States Of America* 90:6325–9 (1993). Abstract Only.
Subramanyam, W.G., et al., "Mechanism Of HIV–1 Tat Induced Inhibition Of Antigen–Specific T Cell Responsiveness", *J. Of Immunol* . 150:2544–2553 (1993). Abstract Only.
Dang, N.H., et al., "Cell Surface Modulation Of CD26 By Anti–1F7 Monoclonal Antibody: Analysis Of Surface Expression And Human T Cell Activation", *J. Of Immunol.* 145:3963–3971 (1990). Abstract Only.
De Caestecker, M.P., et al., "The Detection Of Intercytoplasmic Interleukin 1 (Alpha) Expression In Human Monocytes Using Two Colour Immunofluorescence Flow Cytometry", *J. Immunol. Methods* 154:11–20 (1992). Abstract Only.
Fauci, A.S., "The Human Immunodeficiency Virus: Infectivity And Mechanisms Of Pathogenesis", *Science* 239:617–722 (1988). Abstract Only.
Kinder, D., et al., "Analogues of Carbamyl Aspartate as Inhibitors . . . " *J. Med. Chem,* (1990), 33:819–823.
Snow, R., et al., "Studies on Proline Boronic Acid Dipeptide Inhibityors of Dipeptidyl . . . " *J. Med. Chem,* (1990), 116:10860–10869.
Wijdenes et al., "Monoclonal Antibodies (mAb) against gp130 Imitating Cytokines Which Use the gp130 for Signal Transduction", (Jul., 1995), p. 303.
Blumenstein et al., "Synthetic Non–Peptide Inhibitors of HIV Protease," vol. 163, No. 2 (1989), pp. 980–987.
Luftig et al., "Update on Viral Pathogenesis," ASM News (1990) vol. 56, No. 7, pp. 366–368.
Jiang et al., "Inhibition of Human Immunodeficiency Virus Type 1 Infection in a T–Cell Line (CEM) by New Dipeptidyl–Peptidase IV (CD26) Inhibitors," *Res. Virol.* vol. 148, pp. 255–266, (1997).
Coutts et al., "Structure–Activity Relationships of Boronic Acid Inhibitors of Dipeptidyl Peptidase IV, 1. Variation of the $P_2$ Position of $X_{aa}$–boroPro Dipeptides," *J. Med. Chem.* (1996), vol. 39, pp. 2087–2094.
Ostresh et al., "Generation of Use of Nonsupport–Bound Peptide and Peptidomimetic Combinatorial Libraries," *Methods in Enzymology,* (1996) vol. 267, pp. 220–234.

* cited by examiner cyclic form (cis)

Formula I 448.40

384.75

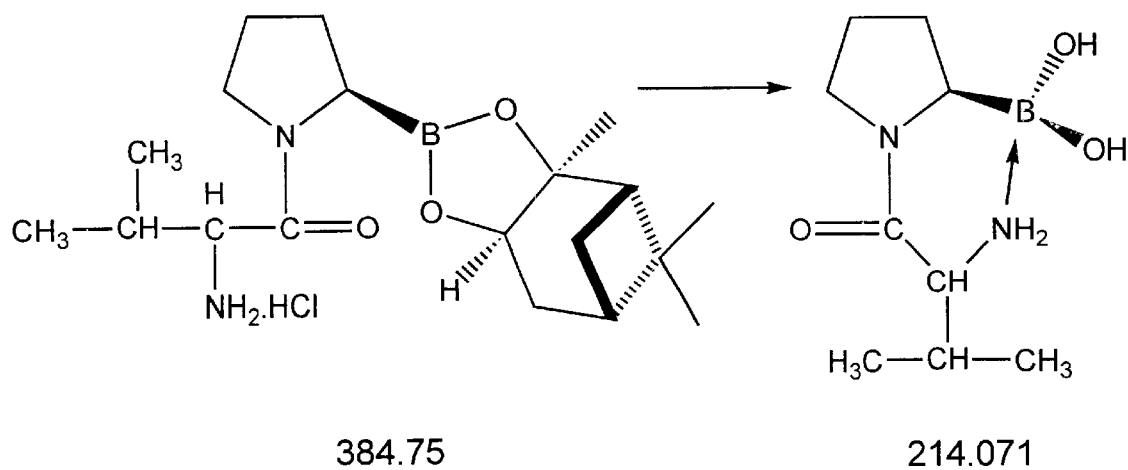
384.75    214.071
FIG. 8
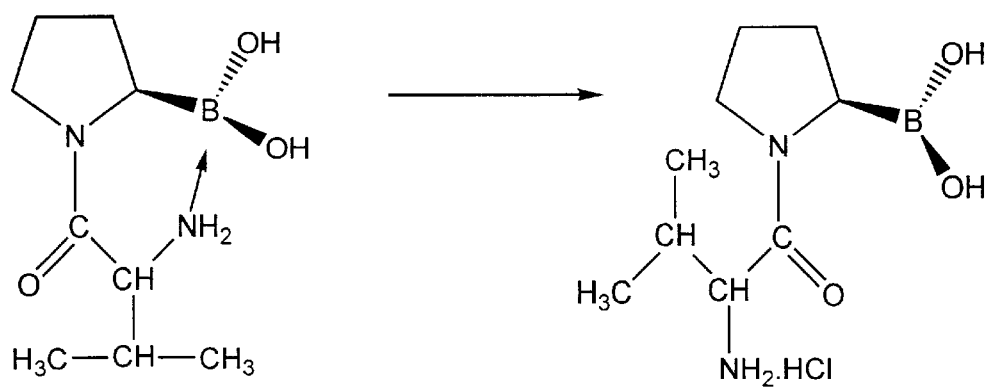
214.07    FIG. 9    250.53

CYCLIC BOROPROLINE COMPOUNDS

RELATED APPLICATION

This application claims priority under Title 35 §119(e), of United States Provisional Application Ser. No. 60/088,540, filed Jun. 5, 1998, and entitled "CYCLIC BOROPROLINE COMPOUNDS," the entire contents of which are incorporated herein by reference.

THE FIELD OF THE INVENTION

This invention relates to substantially pure forms of cyclic boroproline compounds that bind, in cyclic or linear form, to CD26. The invention also relates to methods for using these compounds to stimulate the activation and/or proliferation of CD26-bearing cells to mobilize hematopoietic progenitor cells to spleen and periphery.

BACKGROUND OF THE INVENTION

CD26, a type II transmembrane protein, is expressed on the cell surface of a number of cell types, including lymphocytes (Marguet, D. et al., *Advances in Neuroimmunol.* 3:209–215 (1993)), hematopoietic cells (Vivier, I. et al., *J. Immunol.* 147:447–454 (1991); Bristol, et al., *J. Immunol.* 149:367 (1992)), thymocytes (Dang, N. H. et al., *J. Immunol.* 147:2825–2832 (1991), Tanaka, T. et al., *J. Immunol.* 149:481–486 (1992), Darmoul, D. et al., *J. Biol. Chem.* 267:4824–4833 (1992)), intestinal brush border membrane, endothelial cells, fibroblasts, and stromal cells. Cell surface associated CD26 is a sialoglycoprotein, with most of its mass on the outside of the cell.

CD26 has been best characterized on peripheral T cells where it functions as a potent costimulatory signal for T cell activation. Its surface expression is up regulated upon T cell activation (Dong, R. P. et al., *Cell* 9:153–162 (1996), Torimoto, Y. et al.,*J. Immunol.* 147:2514 (1991), Mittrucker, H-W. et al., *Eur. J. Immunol.* 25:295–297 (1995), Hafler, D. A. et, *J. Immunol.* 142:2590–2596 (1989), Dang, N. H. et al., *J. Immunol.* 144:409 (1990)). CD26 has also been identified in rodents as an important regulatory surface receptor in hematopoiesis and lymphoid development (Vivier, I. et al., *J. Immunol.* 147:447–454 (1991)). The primary structure of CD26 is highly conserved between species (Ogata, S. et al., *J. Biol. Chem.* 264:3596–3601 (1998)). In humans, CD26 reportedly is involved in the regulation of thymocyte activation, differentiation and maturation (Dang, N. H. et al., *J. Immunol.* 147:2825–2832 (1991); Kameoka, J. et al., *Blood* 85:1132–1137 (1995)).

CD26 has an enzymatic activity that is identical to that of Dipeptidyl Peptidase IV (DPP-IV), a serine type exopeptidase with high substrate specificity. It cleaves N-terminal dipeptides from proteins if the penultimate amino acid is proline, or in some cases alanine (Fleischer, B. *Immunol. Today* 15:180 (1994)).

A class of low molecular weight synthetic monomeric molecules with high affinity for CD26 have previously been developed and characterized (G. R. Flentke, et al. Inhibition of dipeptidyl aminopeptidase IV (DP-IV) by Xaa-boroPro dipeptides and use of these inhibitors to examine the role of DP-IV in T-cell function, *PNAS* (USA) 88, 1556–1559 (1991); W. G. Gutheil and W. W. Bachovchin. Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993)). These molecules have been shown to be potent and specific synthetic inhibitors for CD26's associated DP IV proteinase activity. Representative monomeric structures of these transition-state-analog-based inhibitors, Xaa-boroPro, include Pro-boroPro, Ala-boroPro, Val-boroPro, and Lys-boroPro. Boro-Pro refers to the analog of proline in which the carboxylate group (COOH) is replaced with a boronyl group [$B(OH)_2$]. Pro-boroPro, the most thoroughly characterized of these inhibitors has a Ki of 16 picomolar pM) (W. G. Gutheil and W. W. Bachovchin. Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993)). Val-boroPro has even a higher affinity, with a Ki of 1.6 PM (W. G. Gutheil and W. W. Bachovchin. Supra; R. J. Snow, et al. Studies on Proline boronic Acid Dipeptide Inhibitors of Dipeptidyl Peptidase IV: Identification of a Cyclic Species Containing a B—N Bond, *J. Am. Chem. Soc.* 116, 10860–10869 (1994)). Thus, these Xaa-boroPro inhibitors are about $10^{+6}$ fold more potent than the next best known inhibitors.

U.S. Pat. Nos. 4,935,493 (Bachovchin '493) and U.S. Pat. No. 5,462,928 (Bachovchin '928), both of which are incorporated herein by reference, disclose protease inhibitors and transition state analogs (the '493 patent) and methods for treating transplant rejection in a patient, arthritis, or systemic lupus erythematosis (SLE) by administering a potent inhibitor of the catalytic activity of soluble amino peptidase activity of dipeptidyl peptidase type IV (DP-IV; (G. R. Flentke, et al. Inhibition of dipeptidyl aminopeptidase IV (DP-IV) by Xaa-boroPro dipeptides and use of these inhibitors to examine the role of DP-IV in T-cell function, *PNAS* (USA) 88, 1556–1559 (1991)).

PCT published application WO 98/00439 (Multivalent Compounds for Crosslinking Receptors and Uses Thereof) reports that in aqueous solution at all pH values, a boroProline-type CD26 inhibitor exists as a slowly equilibrating mixture of two conformations: an open chain structure which is inhibitory (active species), and a cyclic structure which is non-inhibitory (inactive species). The open, active, inhibitory chain species is favored at low pH while the cyclized structure is favored at high pH. In view of the foregoing, the WO 98/00439 proposes preventing peptide conformational changes, e.g., intermolecular cyclization, by constructing a bivalent or multivalent compound containing an olefin group to form novel CD26 inhibitors. According to WO 98/00439, "if cyclization can be blocked, the inventors predict that the bioavailability of the compounds taught herein can be increased by approximately 100–1000 fold".

SUMMARY OF THE INVENTION

The invention is based upon a variety of surprising and unexpected findings. It has been discovered, unexpectedly, that boro-Pro compounds of the type described in U.S. Pat. No. 4,935,493 (Bachovchin '493) in cyclic form can be orally administered to a subject for treating the same types of conditions for which the linear molecules are useful. It is believed that the cyclic boro-Pro compounds undergo a transformation reaction under acidic conditions in vivo (e.g., stomach) to form a linear reaction product that is capable of selectively binding to CD26 (DP-IV). Thus, according to this aspect, the methods and compositions of the invention are directed to a novel pharmaceutical prodrug, namely, cyclic boro-Proline compounds, for oral administration. Novel compositions containing the substantially pure cyclic boroProline compounds of the invention, in solution or dry form, also are provided.

It is believed that the cyclic compounds of the invention are biologically active in cyclic form, as well as in linear form. Accordingly, the invention also embraces methods and compositions in which the cyclic compounds are administered to a subject or otherwise used in vitro (e.g., screening assays for selection of competitive molecules) in which the cyclic compound is not first subjected to conditions to induce conversion to the linear form. Thus, the cyclic compounds can be administered in oral form (whereby they may or may not be substantially converted to a linear form in the acidic conditions of the stomach), as well as in parenteral form with, or without, prior treatment to convert to the linear form.

The agents useful according to the invention are the cyclic forms of the compounds of Formula I (shown in FIG. 4), including all isomeric forms of this compound (discussed in more detail below. Referring to the Formula I compound, each $X_1$ and $X_2$ is, independently, a hydroxyl group or a group capable of being hydrolyzed to a hydroxyl group in aqueous solution at physiological pH; and X represents a side chain of an amino acid or a peptide which mimics the site of a substrate recognized by a post prolyl cleaving enzyme. In the preferred embodiments, the amino acids are L-amino acid residues (for glycine there is no such distinction); preferably, the C bonded to B is in the L-configuration. By "the C bonded to B is in the L-configuration" is meant that the absolute configuration of the C is like that of an L-amino acid.

Peptides that mimic the substrate binding site of the post-prolyl cleaving enzyme DP IV (also referred to herein as "CD 26") are described in U.S. Pat. No. 4,935,493 ("Bachovchin '493") and U.S. Pat. No. 5,462,928 ("Bachovchin '928").

The open chain (linear form) to cyclic form reaction involves a trans to cis isomerization of the proline and the formation of a new N—B bond. Accordingly, "cyclic form" refers to the cyclized structure of the compounds of formula I that are the boron analogs of a diketopiperazine. This transformation is illustrated in FIG. 3.

By "substantially pure" it is meant that the cyclic compounds of the invention represent at least about 90% by weight of the composition. In the more preferred embodiments, the cyclic boroProline compound represents at least 98% by weight of the composition.

In certain embodiments, the cyclic boroproline compound represents a percentage by weight of the composition selected from the group consisting of at least 5%, at least 10%, at least 20%, at least 30%, at least 40%, at least 50%, at least 60%, at least 70%, at least 80%, at least 90%, at least 95%, at least 96%, at least 97%, at least 98%, at least 99%, and at least 99.5%.

In these and other embodiments, the compositions contain a linear boroProline compound that represents a percentage by weight of the composition selected from the group consisting of a percentage that is less than 95%, less than 90%, less than 80%, less than 70%, less than 60%, less than 50%, less than 40%, less than 30%, less than 20%, less than 10%, less than 5%, less than 4%, less than 3%, less than 2%, less than 1.0%, and less than 0.5.

In a particularly preferred embodiment of the invention, the cyclic boroProline compound is a Val-boroProline compound. A "Val-boroProline compound" refers to a compound of formula I in which the carboxy terminal boroProline is covalently coupled via a peptide linkage in accordance with standard peptide chemistry to a valine amino acid residue. A preferred embodiment is the cyclic form of Val-boroPro, which can be in the following forms: L-Val-S-boroPro, L-Val-R-boroPro, D-Val-S-boroPro, and D-Val-R-boroPro.

More preferably, the compound is L-Val-S-boroPro or L-Val-R-boroPro.

According to yet another aspect of the invention, pharmaceutical compositions and methods for manufacturing such compositions are provided. The pharmaceutical compositions of the invention contain: (1) a pharmaceutically acceptable carrier; and (2) one or more of the cyclic boro-Proline compounds of the invention. Preferably, the pharmaceutical compositions are formulated for oral administration; however, lyophilized forms of the cyclic compounds are also provided for oral or parenteral administration. Such lyophilized or otherwise dried forms of the compounds of the invention may be reconstituted in a buffer of appropriate pH prior to administration. It is believed that oral formations containing the cyclic boroProline compounds of the invention undergo a conformation change from cyclic to linear form following administration, namely, when the compounds are subjected to the acidic pH conditions of the digestive system. For this reason, the preferred oral formations are tablets, capsules, or other solid forms which do not include an enteric coating. The method for manufacturing a pharmaceutical composition involves placing a cyclic boro-Proline compound of the invention in a pharmaceutically acceptable carrier and, optionally, formulating the cyclic compound into a tablet or other form that is suitable for oral administration.

According to another aspect of the invention, methods are provided for modulating immune system function. The compounds of the invention are administered to subjects in need of immune system modulation in amounts effective to modulate immune system function. Modulation of immune system function includes, but is not limited to, increasing immune function such as by stimulating proliferation and specific immune function of immune cells (e.g., CD26-bearing cells) to produce a prophylactic or therapeutic result relating to infectious disease, cancer, and the like. Specific conditions that may be treated according to the invention are deemed specific independent aspects of the invention and are described in detail in the examples. Exemplary conditions that can be treated by administering the compounds of the invention include: HIV infection; neoplasms (wherein the lymphocytes are cytolytic or helper T cells to attack the neoplasm); side effects of chemotherapy or radiation therapy (e.g., resulting from a depletion of cells of the immune system such as a depletion of cells derived from lymphoid, erythroid and/or myeloid lineages); kidney failure (e.g., resulting in depletion of cells of the immune system); bone marrow disorders resulting in immunodeficiency; autoimmunity; and immunodeficiency (e.g., resulting from depletion of cells of the immune system).

More particularly, the compounds of the invention are useful for the stimulation of proliferation, differentiation and mobilization of lymphocytes and hematopoietic cells, as well as for stimulation of cytokine production by stromal cells such as IL-6, IL-11, and G-CSF, and for stabilization or activation of cytokines which are substrates for CD26/DPP-IV protease activity (i.e., the cytokines terminate in the amino acid sequence XaaProline, wherein Xaa is an amino acid, and wherein the peptide sequence is subject to cleavage by CD26/DDP-IV). Accordingly, the invention is useful whenever it is desirable to stimulate the proliferation or differentiation of, or to mobilize, such immune cells, or to stimulate, stabilize or activate cytokine production. Mobilization of hematopoietic cells is characterized by the enrichment of early progenitor cells in the bone marrow and the recruitment of these cells to the periphery in response to a mobilization agent (e.g. G-CSF, GM-CSF, etc.). The agents useful according to the invention can be used to treat lymphocyte and hematopoietic cell deficiencies or to restore hematopoietic and mature blood cell count in subjects with such deficiencies. Such agents also may be used in connection with hematopoietic cell transplants, such as bone marrow or peripheral blood transplants, when used to replenish or create an immune system in a subject. The agents further can be used as an immune booster. The agents also are useful in vitro in connection with the culturing of cells for therapeutic and research uses.

The methods for stimulating activation or proliferation of human lymphocytes, hematopoietic cells, or stromal cells. The method involves contacting the lymphocytes, hematopoietic cells and/or stromal cells, in vivo or in vitro, with an activation or proliferation-inducing concentration of one or more cyclic boroproline compounds of the invention. In certain preferred embodiments, contacting is carried out by orally administering the compound to a human patient in need of such treatment, i.e., the patient is diagnosed as having an adverse medical condition characterized by inadequate lymphocyte or hematopoietic cell activation or concentration. Parenteral administration alternatively can be used to practice the method of treatment on a subject. As used herein, subject means humans, nonhuman primates, dogs, cats, sheep, goats, horses, cows, pigs and rodents.

The compounds of the invention can be administered alone, or in combination with additional agents for treating the condition, e.g., a different agent which stimulates activation or proliferation of said lymphocytes, hematopoietic cells and/or stromal cells. Contacting the lymphocytes with the compounds of the invention can be performed in vitro or in vivo.

As used herein, compound of the invention means the compounds described above as well as salts thereof.

These and other aspects of the invention will be described in greater detail below.

All patents, patent applications, references and other documents that are identified in this patent application are incorporated in their entirety herein by reference.

DEFINITIONS

By "amino acid" is meant to include imino acid.

By "boroPro" is meant an alpha-amino boronic acid analog of proline bonded to an amino acid to form a dipeptide with boroPro as the C-terminal residue. "BoroPro" is used to designate such an analog having the carboxyl group of proline replaced with a $B(OH)_2$ group, where $(OH)_2$ represents two hydroxyl groups and B represents boron.

By Xaa is meant any amino acid residue, e.g., a lysine residue, a valine residue.

"CD26 ligand" is any protein, glycoprotein, lipoprotein or polypeptide that binds to the T cell receptor CD26 and may provide a stimulatory or inhibitory signal.

CD26, Dipeptidyl Peptidase IV (DP IV or DPPIV) and dipeptidyl aminopeptidase IV are used interchangeably. CD26 is a postproline cleaving enzyme with a specificity for removing Xaa-Pro (where Xaa represents any amino acid) dipeptides from the amino terminus of polypeptides.

By alpha-carbon of an amino acid is the one to which the carboxylic acid group is attached. All naturally occurring amino acids are alpha-amino acids or alpha-imino, which means that the amino and carboxylic acid groups are both attached to the same carbon atom.

Each amino acid can be thought of as a single carbon atom (the alpha carbon, C) to which there is attached one carboxyl group, one amino group, a side chain denoted R and a hydrogen, wherein: "R" is a side chain; "$NH_2$" is the alpha amino group; the first carbon (C) attached to the $NH_2$ group having a hydrogen (H) and an R group attached is the alpha carbon; and the carbon double bonded to an oxygen and a hydroxyl group (OH) is the alpha carboxyl group.

The $NH_2$ and COOH groups are used to covalently couple amino acids to one another. The hydroxyl group (OH) of one amino acid on the carboxyl end and the hydrogen (H) on the N terminus are removed ($H_2O$) when two amino acids are linked together. To form a protein, the amino group of one amino acid reacts with the carboxyl group of another by the elimination of water; the resulting chemical bond is called a peptide bond.

By "peptides" is meant a small molecule, e.g., usually containing less than 50 amino acid residues, which do not generally possess a well-defined three-dimensional structure.

Pharmaceutical preparations and modes of administration are described herein.

Other features and advantages of the invention will be apparent from the following detailed description, and from the claims.

BRIEF DESCRIPTION OF THE DRAWINGS

FIG. 8 shows the reaction scheme for the Cyclo-(S)-Val-(R)-boroPro, IP070.

FIG. 9 shows the reaction scheme for the $H_2N$-(S)-Val-(R)-boroPro-OH,HCl,FP020.

DETAILED DESCRIPTION

The invention is based upon a variety of surprising and unexpected findings. It has been discovered, unexpectedly, that boro-Pro compounds of the type described in U.S. Pat. No. 4,935,493 (Bachovchin '493) in cyclic form can be orally administered to a subject for treating the same types of conditions for which the linear molecules are useful. It is postulated that the cyclic boro-Pro compounds undergo a transformation reaction under acidic conditions in vivo (e.g., stomach) to form a linear reaction product that is capable of selectively binding to CD26 (DP-IV). These unexpected results have important therapeutic and experimental research implications. Thus, the methods and compositions of the invention are directed to a novel pharmaceutical prodrug, namely, cyclic boro-Proline compounds, for oral administration. The invention also embraces lyophilized forms of the cyclic boroProline compounds that can be reconstituted in an acidic buffer prior to use to form linear boro-Proline compounds for use in accordance with the methods of the invention. Novel compositions containing the substantially pure cyclic boroProline compounds of the invention, in solution or dry form, also are provided.

Figure 4:
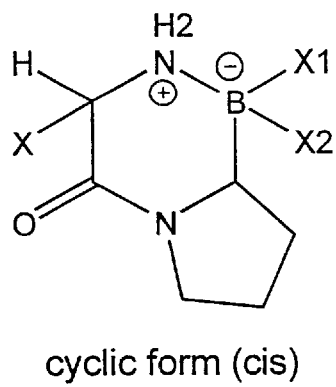
FIG. 4 shows the structure of Formula I.

The agents useful according to the invention are the cyclic forms of the compounds of Formula I (as shown in FIG. 4), wherein each $X_1$ and $X_2$ is, independently, a hydroxyl group or a group capable of being hydrolyzed to a hydroxyl group in aqueous solution at physiological PH; and X represents a side chain of an animo acid or a peptide which mimics the site of a substrate recognized by a post prolyl cleaving enzyme. In the preferred embodiments, the amino acids are L-amino acid residues (for glycine there is no such distinction); preferably, the C bonded to B is in the L-configuration. By "the C bonded to B is in the L-configuration" is meant that the absolute configuration of the C is like that of an L-amino acid.

Thus, the

group has the same relationship to the C as the —COOH group of an L-amino acid has to its α carbon. In some embodiments, X is valine, alanine, or proline residues and the inhibitor, preferably, is L-Val-L-boroPro, L-Ala-L-boroPro; or L-Pro-L-boroPro, or any isomer of the foregoing, respectively.

As used herein, compound of the invention means the compounds described above as well as salts thereof.

Peptides which reportedly have utility for inhibiting post-prolyl cleaving enzymes and which, if coupled to a reactive group, form a covalent complex with a functional group in the reactive site of a post-prolyl cleaving enzyme are described in U.S. Pat. No. 4,935,493, "Protease Inhibitors", issued to Bachovchin et al. ("Bachovchin '493"); U.S. Pat. No. 5,462,928, "Inhibitors of Dipeptidyl-aminopeptidase Type IV", issued to Bachovchin et al. ("Bachovchin '928"); "Proline Derivatives and Compositions for Their Use as Inhibitors of HIV Protease", issued to Hanko et al., ("Hanko '604"); PCT/US92/09845, "Method for Making a Prolineboronate Ester", and its U.S. priority applications (U.S. Ser. Nos. 07/796,148 and 07/936,198), Applicant Boehringer Ingelheim Pharmaceuticals, Inc. ("Boehringer"); and PCT/GB94/02615, "DP-IV-Serine Protease Inhibitors", Applicant Ferring V. V. ("Ferring").

The cyclic boroProline compounds of the invention undergo a conformational change to a linear form ("linear boroproline compounds") that mimics the substrate binding site of the post-prolyl cleaving enzyme DP IV (also referred to herein as "CD 26"). DP IV is a post-prolyl cleaving enzyme with a specificity for removing Xaa-Pro (where Xaa represents any amino acid) dipeptides from the amino terminus of a polypeptide substrate. Representative structures of transition-state analog-based inhibitors Xaa-boroPro, include Val-BoroPro, Lys-BoroPro, Pro-BoroPro and Ala-BoroPro in which "boroPro" refers to the analog of proline in which the carboxylate group (COOH) is replaced with a boronyl group [B(OH)$_2$].

In a particularly preferred embodiment of the invention, the cyclic boroProline compound is a Val-boroProline compound. A "Val-boroProline compound" refers to a compound of formula I in which the carboxy terminal boroProline is covalently coupled via a -peptide linkage in accordance with standard peptide chemistry to a valine amino acid residue. The valine amino acid, optionally, is further coupled via a peptide linkage to additional amino acid residues, provided that the additional amino acid residues do not inhibit the ability of the Val-boroProline compound to bind to CD26. In a most preferred embodiment, the compound of the invention is Val-boroPro (also referred to as "PT-100"). Because of the chiral carbon atoms present on the amino acid residues and on the carbon attached to the boron atom, Val-boroPro can exist in multiple isomeric forms: (a) L-Val-S-boroPro, (b) L-Val-R-boroPro, (c) D-Val-S-boroPro, and (d) D-Val-R-boroPro. More preferably, the compound is L-Val-S-boroPro or L-Val-R-boroPro. In an analogous manner, the other cyclic boroProline compounds of the invention can exist in multiple isomeric forms; however, in general, the forms in which each amino acid chiral center has an "L-" configuration and the boroPro is in the R or S configuration are the preferred forms of the compounds.

Throughout this application, conventional terminology is used to designate the isomers as described below and in appropriate text books known to those of ordinary skill in the art. (See, e.g., Principles in Biochemistry, editor A. L. Lehninger, page 99–100, Worth Publishers, Inc. (1982) New York, N.Y.; Organic Chemistry, Morrison and Boyd, 3rd Edition, Chap. 4, Allyn and Bacon, Inc., Boston, Mass. (1978); See also, Patent Cooperation Treaty published application WO93/10127, application no. PCT/U.S. Ser. No. 92/09845).

All amino acids, with the exception of glycine, contain an asymmetric or chiral carbon and may contain more than one chiral carbon atom. The asymmetric a carbon atom of the amino acid is referred to as a chiral center and can occur in two different isomeric forms. These forms are identical in all chemical and physical properties with one exception, the direction in which they can cause the rotation of plane-polarized light. These amino acids are referred to as being "optically active, i.e., the amino acids can rotate the plane-polarized light in one direction or the other.

The four different substituent groups attached to the α carbon can occupy two different arrangements in space. These arrangements are not super imposable mirror images of each other and are referred to as optical isomers, enantiomers, or stereo isomers. A solution of one stereo isomer of a given amino acid will rotate plane polarized light to the left and is called the levorotatory isomer [designated (−)]; the other stereo isomer for the amino acid will rotate plane polarized light to the same extent but to the right and is called dextrorotatory isomer [designated (+)].

A more systematic method for classifying and naming stereo isomers is the absolute configuration of the four different substituents in the tetrahedryin around the asymmetric carbon atom (e.g., the α carbon atom). To establish this system, a reference compound was selected (glyceraldehyde), which is the smallest sugar to have an asymmetric carbon atom. By convention in the art, the two stereo isomers of glyceraldehyde are designated L and D. Their absolute configurations have been established by x-ray analysis. The designations, Land D, also have been assigned to the amino acids by reference to the absolute configuration of glyceraldehyde. Thus, the stereo isomers of chiral compounds having a configuration related to that of L-glyceraldehyde are designed L, and the stereo isomers having a configuration related to D-glyceraldehyde are designated D, regardless of the direction in which they rotate the plane-polarized light. Thus, the symbols, L and D, refer to the absolute configuration of the four substituents around the chiral carbon.

In general, naturally occurring compounds which contain a chiral center are only in one stereo isomeric form, either D or L. The naturally occurring amino acids are the L stereo isomers; however, the invention embraces amino acids which can be in the D stereo isomer configuration.

Most amino acids that are found in proteins can be unambiguously named using the D L system. However, compounds which have two or more chiral centers may be in $2^n$ possible stereo isomer configurations, where n is the number of chiral centers. These stereo isomers sometimes are designated using the RS system to more clearly specify the configurations of amino acids that contain two or more chiral centers. For example, compounds such as threonine isoleucine contain two asymmetric carbon atoms and therefore have four stereo isomer configurations. The isomers of compounds having two chiral centers are known as diastereomers. A complete discussion of the RS system of designating optical isomers for amino acids is provided in Principles in Biochemistry, editor A. L. Lehninger, page 99–100, supra. A brief summary of this system follows.

The RS system was invented to avoid ambiguities when a compound contains two or more chiral centers. In general, the system is designed to rank the four different substituent atoms around an asymmetric carbon atom in order of decreasing atomic number or in order of decreasing valance density when the smallest or lowest-rank group is pointing directly away from the viewer. The different rankings are well known in the art and are described on page 99 of Lehninger. If the decreasing rank order is seen to be clockwise, the configuration around the chiral center is referred to as R; if the decreasing rank order is counter-clockwise, the configuration is referred to as S. Each chiral center is named accordingly using this system. Applying this system to threonine, one skilled in the art would determine that the designation, L-threonine, refers to (2S, 3R)-threonine in the RS system. The more traditional designations of L-, D-, L-allo, and D-allo, for threonine have been in common use for some time and continue to be used by those of skill in this art. However, the RS system increasingly is used to designate the amino acids, particularly those which contain more than one chiral center.

By "substantially pure" it is meant that the cyclic compounds of the invention represent at least about 90% by weight of the composition. In certain embodiments, the cyclic boroProline compound represents a percentage by weight of the composition selected from the group consisting of at least 5%, at least 10%, at least 20%, at least 30%, at least 40%, at least 50%, at least 60%, at least 70%, at least 80%, at least 90%, at least 95%, at least 30 96%, at least 97%, at least 98%, at least 99%, and at least 99.5%.

In these and other embodiments, the compositions contain a linear boroProline compound that represents a percentage by weight of the composition selected from the group consisting of a percentage that is less than 95%, less than 90%, less than 80%, less than 70%, less than 60%, less than 50%, less than 40%, less than 30%, less than 20%, less than 10%, less than 5%, less than 4%, less than 3%, less than 2%, less than 1.0%, and less than 0.5.

According to yet another aspect of the invention, pharmaceutical compositions and methods for manufacturing such compositions are provided. The pharmaceutical compositions of the invention contain: (1) a pharmaceutically acceptable carrier; and (2) one or more of the cyclic boro-Proline compounds of the invention. In the preferred embodiments, the cyclic boroProline compound is Val-boroPro. Preferably, the pharmaceutical compositions are sterile. The term "pharmaceutically-acceptable carrier" as used herein means one or more compatible solid or liquid filler, diluents or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

Preferably, the pharmaceutical compositions are formulated for oral or parenteral administration; however, lyophilized forms of the cyclic compounds are also provided. Such lyophilized or otherwise dried forms of the compounds of the invention are reconstituted in a buffer of appropriate pH and salt concentration prior to administration. For oral or parenteral administration, the cyclic compounds of the invention are reconstituted in an acidic or neutral buffer prior to administration. For parenteral administration, the cyclic compounds of the invention optionally are reconstituted in an acidic buffer to induce linearization prior to administration. In general, the conditions for reconstitution involve placing the cyclic compound in a buffer having a pH which will allow the cyclic molecule to maintain its conformation upon reconstitution (e.g., oral or parenteral formulations) or which will mediate a conformational change from a cyclic to a linear boro-Proline compound (e.g., oral or parenteral formulations). It is believed that oral formations containing the cyclic boroProline compounds of the invention undergo a conformation change from cyclic to linear form following administration, namely, when the compounds are subjected to the acidic pH conditions of the digestive system. For this reason, certain oral formation embodiments of the invention do not include an enteric coating.

In a related aspect of the invention, a method for manufacturing a pharmaceutical composition is provided. The method involves placing a cyclic boroProline compound of the invention in a pharmaceutically acceptable carrier. Preferably, the pharmaceutically acceptable carrier is suitable for oral administration. More preferably, the method involves formulating the composition into a tablet or capsule which does not include an enteric coating. In yet alternative embodiments, the pharmaceutically acceptable carrier is suitable for parenteral administration and the method further involves lyophilizing (or otherwise drying) the composition to form a lyophilized preparation. Such compositions can be reconstituted by adding to the preparation, a pharmaceutically acceptable carrier having an acidic pH to form a reconstituted preparation for parenteral administration. Alternatively, such composition can be reconstituted by adding to the preparation a pharmaceutically acceptable carrier having a neutral pH (e.g., about pH 6–pH 8, more preferably, from pH 6.5–7.5) to form a reconstituted preparation for oral administration.

According to yet another aspect of the invention, a method for stimulating activation or proliferation of human lymphocytes, hematopoietic cells or stromal cells is provided. The method involves contacting said lymphocytes or hematopoietic cells, in vivo or in vitro, with an activation or proliferation-inducing concentration of one or more cyclic boroproline compounds of the invention. In certain preferred embodiments, contacting is carried out by orally administering the compound to a human patient in need of such treatment, i.e., the patient is diagnosed as having an adverse medical condition characterized by inadequate lymphocyte or hematopoietic cell activation or concentration. Parenteral administration of the reconstituted cyclic compound under conditions to form a linear compound can, alternatively, be used to practice the method of treatment.

The compounds of the invention can be administered alone, or in combination with additional agents for treating the condition, e.g., a different agent which stimulates activation or proliferation of said lymphocytes or hematopoietic cells. For example, the compounds of the invention can be administered in conjunction with exogenous growth factors and cytokines which are specifically selected to achieve a particular outcome. For example, if it is desired to stimulate a particular hematopoietic cell type, then growth factors and cytokines which stimulate proliferation and differentiation of such cell type are used. Thus, it is known that interleukins-1, 2, 3, 4, 5, 6, 7, 9, 10, 11, 12, 13 and 17 are involved in lymphocyte differentiation. Interleukins 3 and 4 are involved in mast cell differentiation. Granulocyte macrophage colony stimulating factor (GMCSF), interleukin-3 and interleukin-5 are involved in the eosinophil differentiation. GMCSF, macrophage colony stimulating factor (MCSF) and IL-3 are involved in macrophage differentiation. GMCSF, GCSF and IL-3 are involved in neutrophil differentiation. GMSCF, IL-3, IL-6, IL-11 and TPO are involved in platelet differentiation. Flt3 Ligand is involved in dendritic cell growth. GMCSF, IL-3, and erythropoietin are involved in erythrocyte differentiation. Finally, the self-renewal of primitive, pluripotent progenitor cells capable of sustaining hematopoiesis requires SCF, Flt3 Ligand, G-CSF, IL-3, IL-6 and IL-11. Various combinations for achieving a desired result will be apparent to those of ordinary skill in the art. Because the agents useful according to the invention stimulate primitive, non-committed hematopoietic progenitor cells, they can be used in connection with any of the foregoing categories of agents to stimulate specifically the proliferation of a particular hematopoietic cell type. The foregoing factors are well known to those of ordinary skill in the art, and most are commercially available.

According to certain embodiments, contacting the lymphocytes with the compounds of the invention can be performed in vitro. For example, any of the following cells can be withdrawn from a patient or cell donor and contacted with a linearized compound of the invention in vitro: T cells, bone marrow cells, stem cells or early lineage progenitor cells from the subject. Preferably, the compounds of the invention are adjusted to neutral pH prior to, or concurrent with, contacting the compounds with the isolated cells in vitro to facilitate formation of the linear boroProline compounds. In this manner, the cyclic compounds can be stored for prolonged periods of time in cyclic form, thereby reducing degradation/enhancing stability of the compounds prior to use. The cells are contacted with amounts of the compounds of the invention that are effective to stimulate the cells; thereafter the treated cells are reintroduced the cells to the patient.

According to another aspect of the invention, methods are provided for modulating immune system function. The compounds of the invention are administered to subjects in need of immune system modulation in amounts effective to modulate immune system function. Modulation of immune system function includes, but is not limited to, increasing immune function such as by stimulating proliferation and specific immune function of CD-26 bearing cells to produce a prophylactic or therapeutic result relating to infectious disease, cancer, and the like. Specifically included is the use of the compounds of the invention for the treatment of disorders characterized by reduced T cell levels in vivo, e.g., HIV and other disorders associated with a compromised immune system. Modulation of immune system function also includes, but is not limited to, decreasing immune function such as by suppressing generally the immune system in transplant recipients or suppressing specifically the immune system to treat autoimmune disease, allergy and the like. In one important embodiment the cyclic boroProline compounds of the invention are used to stimulate blood cell proliferation, as described in detail below. Specific conditions that may be treated according to the invention are deemed specific independent aspects of the invention and are described in detail in the examples. Exemplary conditions that can be treated by administering the compounds of the invention include: HIV infection; neoplasms (wherein the lymphocytes are cytolytic or helper T cells to attack the neoplasm); side effects of chemotherapy or radiation therapy (e.g., resulting from a depletion of cells of the immune system such as a depletion of cells derived from lymphoid, erythroid and/or myeloid lineages); kidney failure (e.g., resulting in depletion of cells of the immune system); bone marrow disorders resulting in immunodeficiency; autoimmunity; and immunodeficiency (e.g., resulting from depletion of cells of the immune system).

The compounds of the invention can be used to stimulate activation or proliferation of human lymphocytes, by contacting the lymphocytes with a proliferation or activation-inducing concentration of the compound in vitro or in vivo. The method preferably involves in vivo administration of the compound, admixed with a pharmaceutically acceptable carrier such as pharmaceutical, sterile saline. The patient can be any patient who suffers from a condition characterized by inadequate lymphocyte activation or concentration. Examples of such conditions are HIV infection, kidney failure, cancer (in particular, cancer accompanied by lymphocyte-depleting chemotherapy), and bone marrow disorders which result in depleted lymphocyte populations in the patient. The compound is preferably administered to the patient orally. Alternatively, the compounds can be used to stimulate proliferation or activation of lymphocytes in vitro, e.g., where a patient's autologous lymphocytes are removed, stimulated to increase activation and/or number of lymphocytes, and reinfused into the patient. This method can be used, for example, to increase the number of cytolytic T cells specific for a patient's tumor or T cells in HIV infected patients.

In one important aspect of the invention, the subject has an abnormally low level of hematopoietic cells or mature blood cells and the agent is administered in an amount effective to restore levels of a hematopoietic cell-type or mature blood cell-type to a preselected normal or protective level. The agent preferably is administered to the subject in at least 2 doses in an 18-hour period. The invention has particularly important applications in the restoration of normal or protective levels of neutrophils, erythrocytes and platelets. The most preferred agent is cyclic ValBoroPro.

According to another aspect of the invention, a method is provided for shortening or eliminating the time that a subject has an abnormally low level of hematopoietic or mature blood cells resulting from treatment with a hematopoietic cell inhibitor. An agent is administered to a subject in need of such treatment in an amount effective to increase the number of hematopoietic cells or mature blood cells in the subject, wherein the administration of the agent begins prior to or substantially simultaneous with administration of the hematopoietic cell inhibitor. The agents and the preferred agent are as described above. In one important embodiment, the hematopoietic cell inhibitor causes an abnormally low level of hematopoietic cells or mature blood cells in the subject and the agent is administered in an amount effective to restore levels of a hematopoietic cell type to a preselected normal or protective level. Preferably, the agent is administered to the subject in at least 2 doses in an 18 hour period. In important embodiments, the agent is used to restore in the subject normal or protective levels of neutrophils, erythrocytes or platelets. The preferred effective amount of agent is as described above.

According to another aspect of the invention, a method is provided for preparing a subject for treatment with a hematopoietic cell inhibitor. The method involves administering to the subject prior to the subject receiving the hematopoietic cell inhibitor an agent in an amount effective to stimulate in the subject production of growth factors. In one embodiment the agent stimulates stromal cell production of growth factor. The agents and the preferred agent are as described above. In one important embodiment, the growth factor is granulocyte colony stimulating factor. In other embodiments the growth factor is selected from the group consisting of IL-1, IL-2, IL-3, IL-4, IL-6, IL-I1, IL-17, TPO, EPO, MCSF, GMCSF, FLT-3 Ligand and Stem Cell Factor. Preferably, the amount administered to the subject is less than 1 mg/kg body weight per day. It also is preferred that the administration of the agent be in at least 2 doses of the agent in an 18 hour period.

According to another aspect of the invention, a method is provided for treating a subject to increase the number of hematopoietic cells or mature blood cells in the subject. An agent is administered to a subject in need of such treatment in an amount effective to increase hematopoietic cells or mature blood cells in the subject, wherein the agent is administered in a first regimen consisting of 2 doses or 3 doses in an 18 hour period. The agents and the preferred agent are as described above. In one important embodiment, the agent is administered in a second regimen consisting of 2 doses or 3 doses in an 18-hour period, wherein the second regimen is separate in time from the first regimen. In another embodiment, the agent is administered in a third regimen consisting of 2 doses or 3 doses in an 18 hour period, wherein the third regimen is separate in time from the first and second regimens. In other embodiments, the agent is administered optionally in a fourth regimen, a fifth regimen, a sixth regimen, or a seventh regimen, wherein each of such regimens consists of 2 doses or 3 doses in an 18 hours period, and wherein the regimens are separate in time from one another and from the prior regimens. In one important embodiment, the subject has an abnormally low neutrophil count and the amount is effective to restore in the subject a preselected level of neutrophils. In other important embodiments the subject has abnormally low levels of erythrocytes and platelets. The preferred dosages, agents, and the like are as described above. In important embodiments, the dosage is no more than six regimens, no more than five regimens, no more than four regimens, no more than three regimens, and even no more than two regimens.

One important aspect of the invention involves restoring or preventing a deficiency in hematopoietic cell number in a subject. Such deficiencies can arise, for example, from genetic abnormalities, from disease, from stress, from chemotherapy (e.g. cytotoxic drug treatment, steroid drug treatment, immunosuppressive drug treatment, etc.) and from radiation treatment.

The invention is useful in general to restore deficiencies created by hematopoietic cell inhibitors. A hematopoietic cell inhibitor is an exogenously-applied agent (such as a drug or radiation treatment) which causes a decrease in the subject of hematopoietic cells and/or mature blood cells.

Hematopoietic cells as used herein refer to granulocytes (e.g. promyelocytes, neutrophils, eosinophils and basophils), erythrocytes, reticulocytes, thrombocytes (e.g. megakaryoblasts, platelet-producing megakaryocytes and platelets), lymphocytes, monocytes, dendritic cells and macrophages. Mature blood cells consist of mature lymphocytes, platelets, erythrocytes, reticulocytes, granulocytes and macrophages. In certain important aspects of the invention, the agents useful according to the invention increase the number of eutrophils, erythrocytes and platelets. In connection with neutrophils, the agents may be used to treat, inter alia, drug or radiation-induced neutropenia, chronic idiopathic neutropenia and cyclic neutropenia.

Stromal cells include fibroblasts, macrophages, endothelial cells, osteoblasts, among other types of cells known to those skilled in the art and described in immunology texts.

One important aspect of the invention is restoring in a subject "normal" or "protective" immune cell levels. A "normal" level as used herein can be a level in a control population, which preferably includes subjects having similar characteristics as the treated individual, such as age. The "normal" level can also be a range, for example, where a population is used to obtain a baseline range for a particular group into which the subject falls. The population can also be divided into groups, such as into quadrants, with the lowest quadrant being individuals with the lowest levels of hematopoietic cells and the highest quadrant being individuals having the highest levels of hematopoietic cells. Thus, the "normal" value can depend upon a particular population selected. Preferably, the normal levels are those of apparently healthy subjects which have no prior history of hematopoietic cell disorders. Such "normal" levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value. Likewise, the level in a subject prior to treatment with a hematopoietic cell inhibitor can be used as the predetermined value.

In general, the normal range for neutrophils is about 1800–7250 per $\mu$l (mean –3650); for basophils 0–150 per $\mu$l (mean –30); for eosinophils 0–700 per $\mu$l (mean –150); for macrophages and monocytes 200–950 per $\mu$l (mean –430); for lymphocytes 1500–4000 per $\mu$l (mean –2500); for erythrocytes $4.2 \times 10^6$–$6.1 \times 10^6$ per $\mu$l; and for platelets $133 \times 10^3$–$333 \times 10^3$ per $\mu$l. The foregoing ranges are at the 95% confidence level.

In connection with certain conditions, the medical community has established certain preselected values. For example, mild neutropenia is characterized as having a count of between 1000 and 2000 per $\mu$l, moderate neutropenia at between 500 and 1000 per $\mu$l and severe neutropenia at below 500 per $\mu$l. Likewise, in adults, a lymphocyte count at less than 1500 is considered a medically undesirable condition. In children the value is less than 3000. Other preselected values will be readily known to those of ordinary skill in the art. The agents useful according to the invention can be used to establish or to re-establish such preselected values, including normal levels.

Protective levels of hematopoietic cells is the number of cells required to confer clinical benefit to the patient. The required levels can be equal to or less than the "normal levels". Such levels are well known to those of ordinary skill in the art. For example, a protective level of neutrophils is above 1000, preferably, at least 1500.

Generally, the compounds of the invention or compositions thereof are useful as immune response modulating therapeutics (1) to treat disease conditions characterized by immunosuppression, e.g., AIDS or AIDS-related complex, other viral or environmentally induced conditions and certain congenital immune deficiencies; (2) to increase an immune function which has been impaired by the use of immunosuppressive drugs, (3) to treat systemic lupus erythematosis, rheumatoid arthritis, and multiple sclerosis.

The compounds of the invention, in cyclic form or following linearization, or compositions thereof can be used to stimulate the growth of hematopoietic cells in culture. Such cells can be transplanted into mammals, e.g., humans, to strengthen or boost the hematopoietic, immune system, or both. These compounds also can be used to treat patients suffering from disease or from deficiency of hematopoietic cells such as AIDS patients, patients undergoing chemotherapy and/or patients under radiotherapy for hematological or other cancers, and patients undergoing bone marrow transplants.

When administered to mammals, e.g., humans, the compounds of the invention may enhance the ability of the immune system to regenerate cells that are suppressed, e.g., CD4 and T cells. Thus, the compounds of this invention, can be administered to mammals, e.g., humans, in an effective amount alone or in combination with a pharmaceutically acceptable carrier, excipient, or diluent, in unit dosage form. Conventional pharmaceutical practice can be employed to provide suitable formulations or compositions to administer these compounds to patients suffering from immunosuppression or an immune deficiency or presymptomatic of AIDS. Any appropriate route of administration may be employed, for example, parenteral, intravenous, subcutaneous, intramuscular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols. As noted above, compounds which are orally administered do not require adjustment of the pH to acidic conditions to form the linear compound prior to administration in view of the acidic environment of the digestive system.

The compounds of the invention or compositions thereof can be used to control the T cell activation process and thus be used to prevent unwanted immune responses. The compounds of the invention or compositions thereof can be used to enhance recall-antigen specific immune responses. Lymphocytes from most HIV-infected individuals exhibit a qualitative defect in their ability to respond to recall antigens (A. S. Fauci. The human immunodeficiency virus: infectivity and mechanisms of pathogenesis. *Science* 239, 617–722 (1988)). This defect is exhibited early after infection and long before CD4+T cell number decline. Accordingly, it is believed that these compounds will be useful in treating AIDS. Thus, the stimulatory activities should improve lymphocyte function in HIV infected individuals by ameliorating the defective recall antigen responses which show up early after infection, and by improving CD4+T cell numbers.

Since it is believed that the compounds of the invention, in cyclic or linear form, have high affinity and specificity for CD26, they can be useful for the selective delivery of other therapeutic agents to, and into all CD26-bearing cells, e.g., CD4+T cells. Thus, the compounds of the invention can be used to deliver pharmacological agents inside CD26-bearing cells that normally are unable to penetrate such cells. For example, many highly potent inhibitors of the HIV protease have been developed, which despite their high affinities for the HIV proteinase, are limited in blocking HIV in vivo owing to their inability to get inside the CD26-bearing cells. These HIV proteinase inhibitors can be linked to a compound of the invention (e.g., via covalent attachment to an amino acid side chain or functional group in the non-CD26 binding portion of the molecule (the amino terminus), provided the attachment does not adversely affect the ability of the compound to cyclize at neutral pH) and delivered into CD26+ cells. Even if a drug is capable of entering CD26+ cells, the compounds of the invention can be used to concentrate the drug in CD26+ cells, thereby maximizing the desired pharmacological activity while minimizing unwanted toxic side effects on other cells. This delivery vehicle therefore provides a mechanism to prevent lysis of HIV infected cells, e.g., by delivering AZT to CD26+ cells. Thus, the CD26 internalization activity of the compounds disclosed herein can be used to provide a vehicle for delivering and concentrating other therapeutic agents into CD26-bearing cells.

The compounds of the invention or compositions thereof can be administered alone or in combination with one another, or in combination with other therapeutic agents. For example, treatment with one or more of the compounds of the invention can be combined with more traditional therapies for treating disorders of the immune system.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. The pharmaceutical compositions also may contain, optionally, suitable preservatives, such as: benzalkonium chloride; chlorobutanol; parabens and thimerosal. Carrier formulation suitable for oral, subcutaneous, intravenous, intramuscular, etc. administrations can be found in Remington's Pharmaceutical Sciences, Mack Publishing Co., Easton, Pa.

A variety of administration routes are available for treating a subject. The particular mode of delivery selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. Such modes of administration also include obtaining T cells or bone marrow cells, stem cells or early lineage progenitor cells from a patient and contacting the isolated cells with the compounds of the invention ex vivo, followed by reintroducing the treated cells to the patient. The treated cells can be reintroduced to the patient in any manner known in the art for administering viable cells.

Oral administration is particularly preferred. Compositions suitable for oral administration may be presented as discrete units, such as capsules, tablets, lozenges, each containing a predetermined amount of the compound of the invention. Other compositions include suspensions in aqueous liquids or non-aqueous liquids such as a syrup, elixir or an emulsion. Preferably, the oral preparation does not include an enteric coating since it is desirable to expose the cyclic compounds of the invention to the acidic pH conditions of the digestive tract to convert the cyclic molecules to their linear counterparts.

As used herein, the term "parenteral" includes subcutaneous, intravenous, intramuscular, or infusion. Compositions suitable for parenteral administration conveniently comprise a sterile aqueous preparation of the compound, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Intravenous or intramuscular routes are not particularly suitable for long-term therapy and prophylaxis. They could, however, be preferred in emergency situations. Oral administration will be preferred for prophylactic and other treatment because of the convenience to the patient as well as the dosing schedule.

The pharmaceutical compositions may conveniently be presented in unit dosage form and may be prepared by any of the methods well-known in the art of pharmacy. The methods include the step of bringing the compounds of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, as used herein, means that the implant is constructed and arranged to delivery therapeutic levels of the active ingredient for at least 10 days, and preferably 60 days. Long-term sustained release implants are well-known to those of ordinary skill in the art and include some of the release systems described above.

The compounds described herein are administered in effective amounts. An effective amount is a dosage of the compound sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, an effective amount for stimulating T cell activation or hematopoiesis would be an amount sufficient to increase to a statistically significant extent T cell activation or hematopoiesis as for example, measured by increased cell numbers or by increased T cell activity. An effective amount for stimulating a desired immune response also can be measured, for example, by determining a change in the immune function in a subject (e.g., increased B cell response, increased cytotoxic T cell response, stimulation of bone marrow cell proliferation, increase in white or red blood cells, or an ability to slow, halt, or prevent an infection or cancer). An effective amount for treating an autoimmune disorder or allergic disorder would be that amount sufficient to lessen or inhibit altogether the immune or allergic response associated with the disorder so as to slow or halt the development of or the progression of the disorder. Thus, it will be understood that the compounds of the invention can be used to treat an autoimmune disorder (e.g., transplant rejection) prophylactically in subjects at risk of developing an immune response (e.g., recipients prior to transplant). As used in the claims, "inhibit" embraces all of the foregoing. Likewise, an effective amount for treating an immune system disorder is that amount which can slow or halt altogether the symptoms associated with the immune system disorder so as to prevent the disorder, slow its progression, or halt the progression of the immune system disorder. It is preferred generally that a maximum dose be used, that is, the highest safe dose according to sound medical judgment.

Generally, doses of active compounds will be from about 0.001 mg/kg per day to 1000 mg/kg per day. It is expected that doses range of 0.001 to 100 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

All patents, patent applications, references and other documents that are identified in this patent application are incorporated in their entirety herein by reference.

EXAMPLES

The working examples demonstrate the oral bioavailability of a representative cyclic compound of the invention and the functional activity of this compound with respect to stimulating the proliferation of lymphocytes in vivo. The examples are illustrative only and are not intended to limit the invention in any way. A particularly preferred compound of the invention, cyclic Val-boroPro ("PT-100"), is used in the working examples.

Throughout this application and in particular, in each of the Examples and drawings, particular embodiments are described and illustrated. It is to be understood that any of the reactive groups disclosed herein can be substituted for the particular reactive groups (e.g., boronyl group) shown in the drawings or described in the particular Examples. Formation of the cyclic compounds can be assessed, e.g., by NMR.

EXAMPLE 1

GENERAL SYNTHESIS OF COMPOUNDS

The synthesis of the compounds of the invention involves very similar chemistry. These compounds are designed such that they selectively bind to the CD26 receptor. Synthesis of the linear boroproline compounds are described in Bachovchin '493. Conversion of the linear boroProline compounds to the cyclic boroProline compounds of the invention is accomplished by placing the linear compounds under conditions of neutral pH (about pH 6 to about pH 8.0, more preferably, about 6.5 to about 7.5) for a time sufficient to effect the above-described conformational change from linear to cyclic form. Conversely, under acidic conditions, the cyclic form undergoes a conformational change to linear form. It is believed that both the cyclic and linear forms of these compounds are biologically active (bind to the CD26 receptor) and that linearization is not required for biological or binding activity. Accordingly, the cyclic compounds can be administered without prior treatment to induce a conformational change to the linear form.

For the most part, straightforward peptide coupling chemistry is employed to prepare the linear boroProline compounds. The standard peptide coupling chemistry methods and procedures used in this invention are readily available. Examples of books using these methods include, but are not limited to, the following citations incorporated herein by reference: P. D. Bailey, *An Introduction to Peptide Chemistry*, Ed.: John Wiley & Sons, 1990; Miklos Bodansky, *Peptide Chemistry A Practical Textbook*, Ed.: Springer-Verlag, 1988; Miklos Bodansky, *Principles of Peptide Synthesis*, "Reactivity and Structure Concepts in Organic Chemistry," Volume 16, Ed.: Springer-Verlag, 1984; and Miklos Bodansky, *Principles of Peptide Synthesis*, "Reactivity and Structure Concepts in Organic Chemistry," Volume 21, Ed.: Springer-Verlag, 1984.

The compounds of the invention can begin with the synthesis of H-boroPro as taught in WO 98/00439. Use of H-boroPro is for illustrative purposes only, and is not intended to limit the scope of this invention.

According to WO 98/00439, H-boroPro was prepared by the synthetic route previously developed and described (G. R. Flentke, et al., "Inhibition of dipeptidyl aminopeptidase IV (DP-IV) by Xaa-boroPro dipeptides and use of these inhibitors to examine the role of DP-IV in T-cell function," PNAS (U.S.A.) 88, 1556–1559 (1991); also described in U.S. Pat. No. 5,462,928). Alternatively, H-boroPro may be produced by a new procedure (Kelly, T. A., et al., "The efficient synthesis and simple resolution of a proline boronate ester suitable for enzyme inhibition studies," Tetrahedron 49, 1009–1016 (1993)). Both of these synthetic routes reportedly yield racemic H-boroPro pinanediol.

According to WO 98/00439, stereochemically pure L, L and L, D diastereomers of Z-Lys-boroPro were prepared by first resolving racemic H-boroPro through crystallization with optically active blocking protecting groups ((1S, 2S, 3R, 5S)-+-pinanediol isomer) followed by coupling the isotopically pure L-boroPro and D-boroPro to the stereochemically pure L isomer of lysine (See U.S. Pat. No. 5,462,928). Alternatively, the L,L and L,D diastereomers of Lys-boroPro were prepared in high optical purity by coupling racemic H-boroPro by L-Lys and separating the resulting diastereomeric Z-Lys-boroPro-diester into its component L,D and L,L diastereomers using reverse phase HPLC as previously described for diastereomeric Pro-boroPro (W. G. Gutheil and W. W. Bachovchin, "Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition," Biochemistry 32, 8723–8731 (1993)). A specific protocol for obtaining a preferred compound of the invention is provided in Example 7.

EXAMPLE 2

CYCLIZATION REACTION

Identification of Active (Open) and Inactive (Cyclic) Species of Monomeric Compounds as Related to Inhibitory Activity of Soluble CD26 (DP IV)

Figure 3:
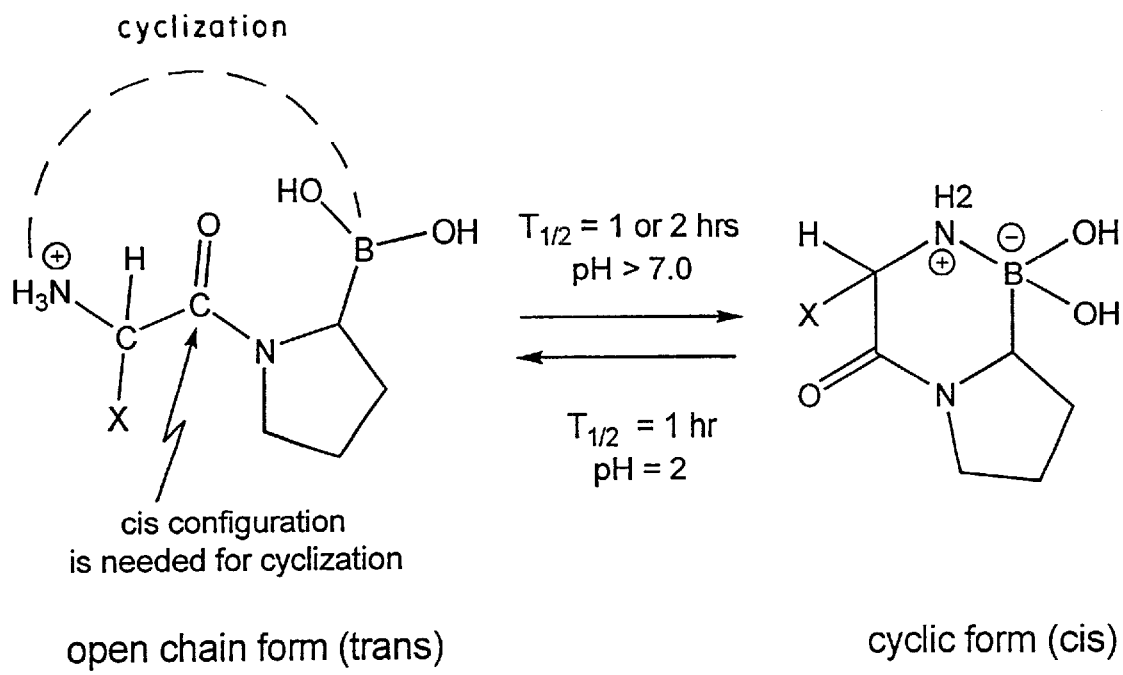
FIG. 3 shows the structures of the open and cyclized forms of Xaa-boroPro inhibitors (conformational equilibrium of Xaa-boroProline inhibitors).

In aqueous solution at all pH values, the inhibitors exist as a slowly equilibrating mixture of two conformations: an open chain structure (linear boroproline compound) which is inhibitory (active species), and a cyclic structure (cyclic boroProline compound) which is non-inhibitory (inactive species). See FIG. 3 which is a diagram showing the structures of the open and cyclized forms of Xaa-boroPro inhibitors (conformational equilibrium of Xaa-boroproline inhibitors). The open, active, inhibitory chain species is favored at low pH while the cyclized structure is favored at neutral pH. The reaction is fully reversible: the open chain becomes predominant at low pH. The open chain to cyclic species reaction involves a trans to cis isomerization of the proline and the formation of a new N—B bond. The cyclized structure is the boron analog of a diketopiperazine, a product often seen in peptide chemistry.

Cyclization liberates one equivalent of H+ thereby explaining the requirement for base in the cyclization reaction and acid in the opening reaction. The cyclic structure is quite stable in aqueous solutions of high pH.

Prolonged incubation at high pH never leads to the complete disappearance of DP IV inhibitory activity for any of the Xaa-boroPro compounds examined. This observation was the first evidence that the active inhibitor was in a conformation equilibrium with a non-inhibitory species rather than undergoing an irreversible inactivation. The half life for the reformation of the open chain species from the cyclic structure is surprisingly low. Thus, it was concluded that the loss of inhibitory activity in aqueous solution was due to a pH dependent conformational equilibrium rather than a degradation reaction.

The fact that the inhibitory activity does not go to zero for any of the Xaa-boroPro inhibitors, even after prolonged incubation, together with the fact that the reverse reaction, i.e., cyclic to open chain is slow, suggested that it should be possible to measure the equilibrium constant for the conformation equilibrium by measuring the apparent Ki at equilibrium and comparing it with the true Ki. It has been reported that the ratio of [cyclic]: [open] forms, at neutral pH, is 156:1 for Pro-boroPro and 11:30 for Val-boroPro (W. G. Gutheil and W. W. Bachovchin, Separation of L-Pro-DLboroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993)). This means that less than 1% Pro-boroPro and less than 0.1% of Val-boroPro exists as the open chain, inhibitory species, at equilibrium at pH 7.0. Nevertheless, under these conditions the inhibitors behave as though they had Ki's of 2.5 nM and 1.8 nM respectively. This apparent Ki of the "filly inactivated" species is still substantially better than, (~1000-fold) that of other inhibitors of DP IV thus far reported.

The inventors believe that the cyclic compounds of the invention have the ability to specifically bind to CD26. Accordingly, the inventors predict that the biological function of the compounds of the invention could be significantly increased (approximately 100–1000 times) by orally administering the cyclic compounds of the invention and permitting the conformational changes, e.g., linearization, to occur in vivo (e.g., under the acidic conditions of the stomach). Thus, if linearization is necessary, it can be accomplished in vivo and therefore, therapeutic concentrations in the systemic circulation can be generated in situ and, accordingly, it is believed that the bioactivity of the compounds of the invention can be increased by approximately 100–1000 fold. In addition, it is believed that the cyclic boroProline compounds of the invention, in lyophylized or solid form, have improved shelf life properties, thereby contributing to the further utility of the compounds of the invention.

Each of the compounds prepared as described above can be purified to homogeneity using HPLC and its identity can be confirmed by NMR spectroscopy, amino acid composition, or mass spectroscopy as deemed necessary.

The cyclic compounds of the invention can be converted to linear form by adjusting the pH to an acidic pH (e.g., pH range: 1–3) and the potency of inhibition of CD26 proteinase activity by the linear boroProline compounds can be determined using conventional enzyme analysis (example provided below). In addition, the immunomodulatory effects of the compounds of the invention are evaluated by in vivo experiments using animal models and by in vitro experiments using cell culture methods that are believed by those of ordinary skill in the art to be predictive of an in vivo activity.

EXAMPLE 3

ASSESSMENT OF FUNCTIONAL ACTIVITY

The compounds of the invention have at least the following properties: (i) binding site is the DP IV active site; and (ii) exhibit cross-species specificity.

The assays which are used to assess functional activity include: DPIV (also referred to as "DPPIV") activity, oral bioavailability and neutrophil proliferation assays and are described in detail below. The cyclic compounds may be converted to linear form prior to performing the activity assays or assayed directly without prior conversion.

EXAMPLE 4

MEASURING STANDARD CD26 (DP IV) ACTIVITY

Assays to measure CD26 (DP IV) activity can be performed on the compounds of the invention. Methods for quantitatively measuring the interaction of small peptidomimetic inhibitors with CD26 or DP IV, as well as for the interaction of CD26 with larger ligands, e.g., the HIV Tat protein, have been developed (W. G. Gutheil and W. W. Bachovchin.

Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993); Gutheil, W. G., and W., B. W. Kinlsq, A Matlab Program for Fitting Kinetics Data with Numerically Integrated Rate Equations and Its Application to the Analysis of Slow, Tight Binding Data, Analytical Biochemistry 223, 13–20 (1994); Gutheil, W. G., et al., HIV-1 Tat Binds to DP IV (CD26): A possible Mechanism for Tat's Immunosuppressive Activity, *Proc. Natl. Acad. Sci. U.S.A.* 91, 6594–6598 (1994)). These methods use the chromatogenic substrate Ala-Pro-p-nitroanilide (AppNA) and fluorescent substrate Ala-Pro-7-amino-4-trifluoromethyl coumarin (AP-AFC). AppNA and AP-AFC are commercially available (e.g., Enzyme Systems Products, Dublin, Calif.).

EXAMPLE 5

MEASURING ORAL BIOAVAILABILITY

Figure 1:
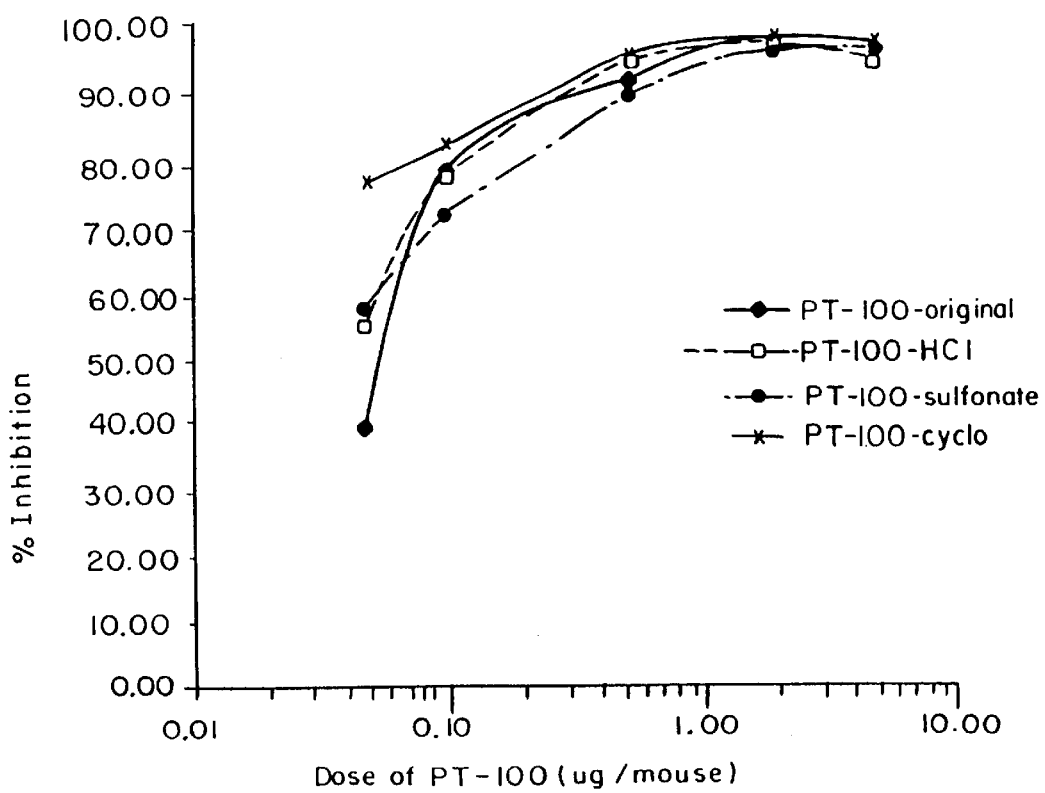
FIG. 1 shows the oral bioavailability of cyclic PT-100 and the HCl and methane sulfonate salts of PT-100.

The data for this example appears in FIG. 1.

Various samples of PT-100 were administered as 0.2 ml of a solution in 0.9% (w/v) saline by oral gavage to BALB/c mice at the doses indicated on the X-axis of FIG. 1. Two hours later blood samples were withdrawn individually from the tails of the mice, and the DPPIV activity of each sample was measured in the fluorometric assay. The data are expressed on the Y-axis of FIG. 1 as the % inhibition of the DPPIV activity in serum samples collected from mice gavaged with 0.2-ml saline without compound. The mean and standard deviation of samples from three animals have been plotted for each data point.

EXAMPLE 6

STIMULATION OF NEUTROPHIL PROLIFERATION

Figure 2:
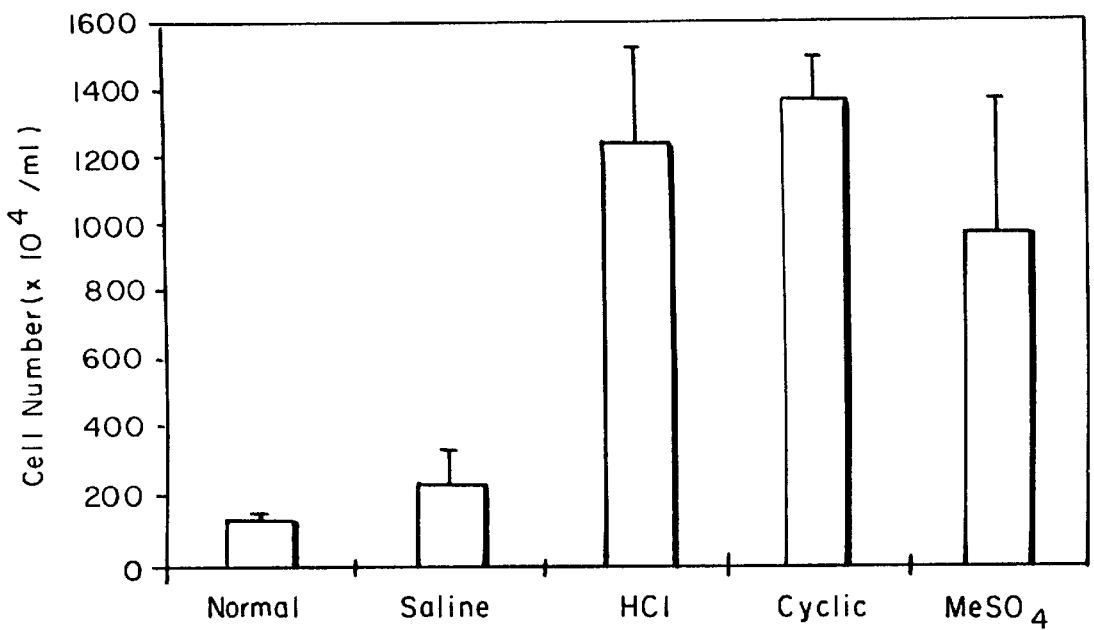
FIG. 2 shows the effect of cyclic PT100 and the Chl and methane sulfonate salts of PT-100 on the regeneration of neutrophils in cyclophosphamide treated mice.

The data for this example appears in FIG. 2.

On day-0, female BALB/c mice of 6–8 weeks of age were injected intraperitoneally with cyclophosphamide at a dose of 220 mg/kg. Normal controls received an injection of water, the vehicle alone. Commencing on day-3 and continuing through day-7, each form of Val-boroPro (VBP) was administered twice daily by oral gavage using a dose of 2 μg/mouse for each administration. The different forms of VBP used were: HCl=linear, the HCl salt; Cyclic=free base, not salt; and MeSO4=linear, the methylsulfonate salt. Solutions of the different forms of VBP were prepared in 0.1 N HCl and stored as frozen aliquots at −20° C. An aliquot of each form was thawed on day-3 and the thawed aliquots were then kept at 4° C. for the duration of the dosing period. Normal and saline control groups received saline only by the same regimen. Groups of four replicate mice were used for each dose of each form of VBP and the control treatments.

On day-7, individual blood samples were collected from the tails of each mouse into EDTA-containing microtainer tubes. The data shown represent the mean (+/− standard deviation) of absolute neutrophil counts calculated from a different count of peripheral blood smears stained with Wright Giemsa, and a total white cell count performed in a hemocytometer after the lysis of erythrocytes with 0.5% acetic acid.

EXAMPLE 7

SPECIFIC SYNTHESIS PROTOCOL

Figure 5:
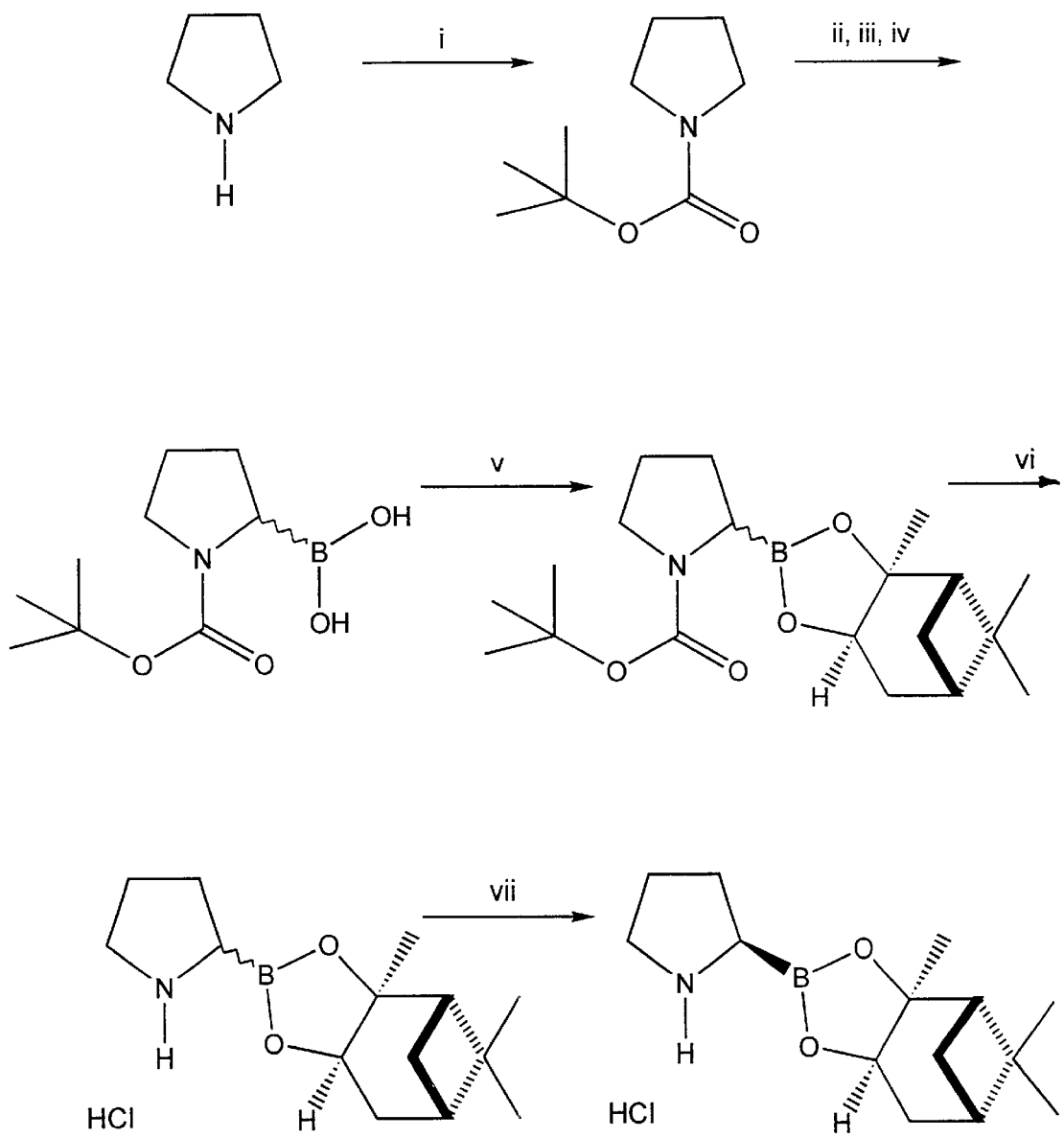
FIG. 5 shows the reaction scheme for the proposed boronoproline synthetic route.

The reaction schemes for this example are provided in FIG. 5.

EXAMPLE 7A

Proposed Boronoproline Synthetic Route

The reaction scheme for this protocol is shown in FIG. 5, wherein the Reagents and Conditions are as follows: I. di-t-butyl dicarbonate, dichloromethane; ii. s-butyllithium tetramethylethylethylenediamine; iii. trialkylborate (alkyl= methyl, ethyl, or butyl), ether; iv. Dilute aqueous hydrochloric acid; v. pinanediol, ether; vi. anhydrous hyudrochloric acid, ethyl acetate; vii. recrystallization.

References

S. J. Couttes et al. *J. Med. Chem.* 1996, 39, 2087; T. A. Kelly et al. *Tetrahedron Letters* 1993, 49, 1009; P. Beak et al. *Tetrahedron Letters* 1989, 30, 1197; and F. R. Bean et al. *J. Amer. Chem. Soc.* 1932, 54, 4415.

EXAMPLE 7B

B-BOC-(S)-Val-(R)-boroPro-(1S,2S,3R, 5S)-pinanediol ester, IP068

Figure 6:
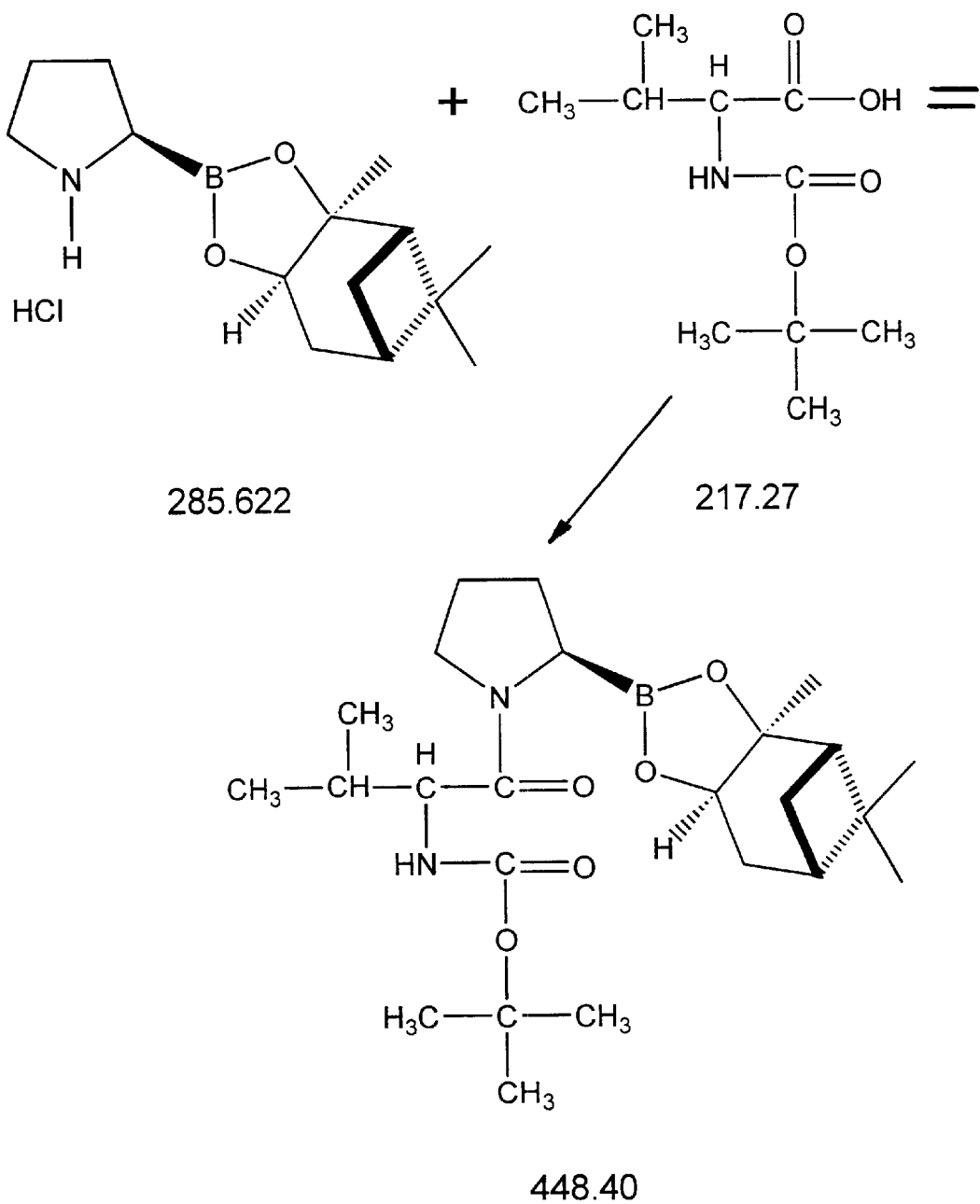
FIG. 6 shows the reaction scheme for the N-BOC-(S)-Val-(R)-boroPro-(1S,2S,3R,5S)-pinanediol ester, IP068.

The reaction scheme for this protocol is shown in FIG. 6.

The mass of starting material, (1S,2S,3R,5S)-pinanediol Pyrrolidine-2R*-Boronate HCl, equals ":A". The reaction scheme for this protocol is as follows:

1. Charge $CH_2C_1$ (A×20 mL/g)
2. Charge BOC-valine (A×0.761 g/g)
3. Cool to 0–5° C.
4. Charge hydroxybenzotriazole (A×0.473 g/g)
5. Charge EDCI (A×0.874 g/g) FW=191.71 (EDCI is "1-(3-Dimethylaminopropyl)-3-ethylcarbodiimide hydrochloride")
6. Stir for 30 minutes at 0–5° C.
7. Charge (1S,2S,3R,5S)-pinanediol Pyrrolidine-2R*-Boronate HCl (amount=A)
8. Charge 4-Methylmorpholine (A×0.722 mL/g)
9. Allow to warm slowly to room temperature
10. Stir overnight
11. Wash with water (A×9.5 mL/g)
12. Wash with 1M $KHSO_4$ (A×9.5 mL/g)
13. Wash with Sat'd $Na_2CO_3$ solution (A×9.5 mL/g)
14. Dry over $MgSO_4$
15. Filter through a plug of silica gel, eluting with EtOAc(A×0.1 L/g)
16. Concentrate to dryness
17. Theory=A×1.57 g/g expect=theory×(95 to 98%)
Observed Yield: 84%

EXAMPLE 7C

HEN-(S)-Val-(R)-boroPro-(1S,2S,3R,5S)-pinanediol ester, HCl IP069

Figure 7:
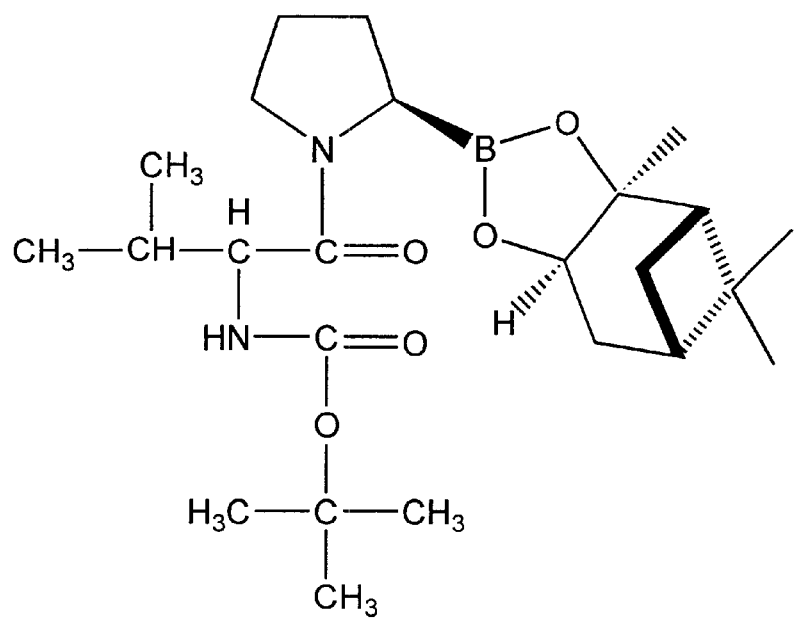
FIG. 7 shows the reaction scheme for the $H_2N$-(S)-Val-(R)-boroPro-(1S,2S,3R,5S)-pinanediol ester, HCl IP069.
Figure 7:
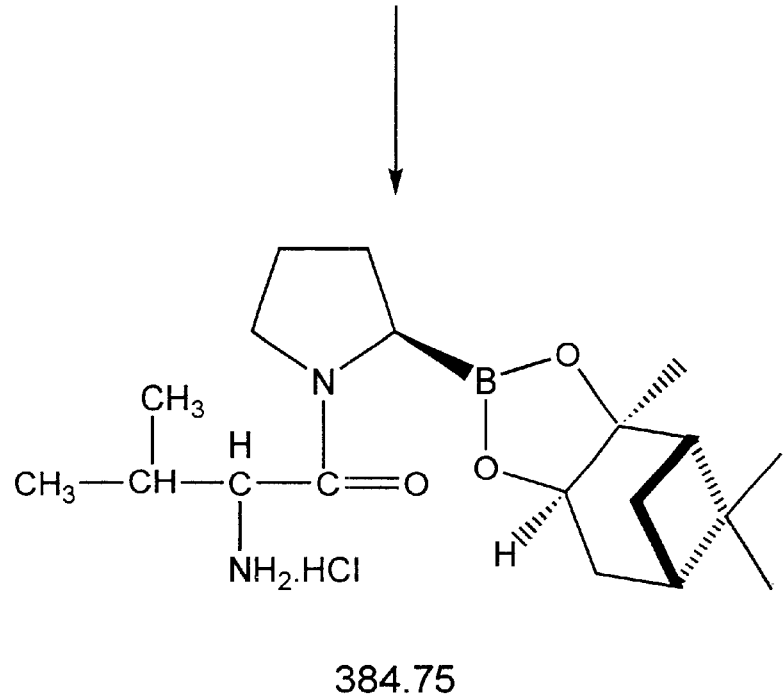

The reaction scheme for this protocol is shown in FIG. 7 and is as follows:

1. Charge 1M HCl in $Et_2O$ (A×37.2 mL/g) to a flask
2. Bubble anhydrous HCl into the solution for 10 min
3. Cool to 0–5° C.
4. Charge N-BOC-(S)-Val-(R)-boroPro-(1S,2S,3R,5)-pinanediol ester, IP068 (amount=A)
5. Stir overnight, allowing mixture to warm slowly to room temperature.
6. Concentrate to dryness
7. Theory=A×x0.858 Expect≅100%
Observed Yield: 106%

EXAMPLE 7D

Cyclo-(S)-Val-(R)-boroPro, IP070

The reaction scheme for this protocol is shown in FIG. 8 and is as follows:

1. Charge $H_2N$-(S)-Val-(R)-boroPro-(1S,2S,3R,5S)-pinanediol ester, HCl (Amount=A) to a flask
2. Charge $H_2O$ (A×25 mL/g)
3. Adjust pH to 2 with 1N HCl (if necessary)
4. Charge Hexane (A×25 mL/g)
5. Charge phenyl boronic acid (A×0.333 glg)
6. Stir vigorously
7. Decant hexane layer and replace with fresh hexane after 30 minutes
8. Again replace hexane layer after 60 minutes
9. Replace hexane layer after 90 minutes
10. Replace hexane layer after 120 minutes
11. Stir overnight
12. Separate the layers
13. Load aqueous layer on prepared Dowex 50-X2–100 ion exchange column (H*form)
14. Elute with $H_2O$ until neutral
15. Elute with 1:50 $NH_4OH:H_2O$
16. Lyophilize appropriate* fractions
17. Theory=A×0.556 g/g expect 90 to 95%
Observed Yield: 83%

* TLC: 1:50 $NH_4OH$:MeOH Product visualized using $I_2$ chamber.

EXAMPLE 7E $H_2N$-(S)-Val-(R)-boroPro-OH, HCl, FP020

The reaction scheme for this protocol is shown in FIG. 9 and is as follows:

1. To Cyclo-(S)-Val-(R)-boroPro, IP070, charge 51.4 mL/g of 0.1 N HCl
2. Stir 10 min
3. Lyophillize the product
Theory=g IP070×1.17 g/g Expect≅100%
Observed Yield: 106%

Other embodiments are within the following claims. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

We claim:

1. A pharmaceutical composition comprising,
    (1) a substantially pure preparation of a cyclic boroProline compound having the structure of formula I

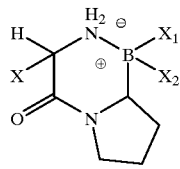

wherein each $X_1$ and $X_2$ is, independently, a hydroxyl group or a group capable of being hydrolyzed to a hydroxyl group in aqueous solution at physiological pH; and X represents a side chain of an amino acid or a peptide which mimics the site of a substrate recognized by a post prolyl cleaving enzyme; and
    (2) a pharmaceutically acceptable carrier.

2. The composition of claim 1, wherein the cyclic boro-Proline compound is selected from the group consisting of L-Val-S-boroPro, L-Val-R-boroPro, D-Val-S-boroPro, and D-Val-R-boroPro.

3. The composition of claim 1, wherein the cyclic boro-Proline compound is selected from the group consisting of L-X-S-boroPro, L-X-R-boroPro, D-X-S-boroPro, and D-X-R-boroPro, wherein L-X is an amino acid in an L configuration or a peptide containing amino acids in an L configuration.

4. A method for manufacturing a pharmaceutical composition comprising:
    placing a compound of claim 1 in a pharmaceutically acceptable carrier.

5. The method of claim 4, wherein the pharmaceutically acceptable carrier is suitable for oral administration.

6. The method of claim 5, further comprising the step of formulating the composition into a tablet or capsule which does not include an enteric coating.

7. The method of claim 4, wherein the pharmaceutically acceptable carrier is suitable for parenteral administration.

8. The method of claim 7, further comprising the step of lyophilizing the composition to form a lyophilized preparation.

* * * * *